United States Patent [19]

Janssens et al.

[11] Patent Number: 4,556,660

[45] Date of Patent: Dec. 3, 1985

[54] N-(BICYCLIC HETEROCYCLYL)-4-PIPERIDINAMINES

[75] Inventors: Frans E. Janssens, Bonheiden; Joseph L. G. Torremans, Beerse; Jozef F. Hens, Nijlen; Theophilus T. J. M. Van Offenwert, Vosselaar, all of Belgium

[73] Assignee: Janssen Pharmaceutica N.V., Beerse, Belgium

[21] Appl. No.: 487,774

[22] Filed: Apr. 22, 1983

Related U.S. Application Data

[63] Continuation-in-part of Ser. No. 397,626, Jul. 12, 1982, abandoned.

[51] Int. Cl.[4] .................. C07D 401/12; A61K 31/445

[52] U.S. Cl. .................... 514/272; 544/331; 544/316; 544/328; 544/238; 544/333; 544/295; 544/296; 544/284; 544/353; 544/405; 544/224; 544/55; 544/298; 546/118; 546/187; 546/193; 546/199; 546/174; 546/171; 546/172; 546/153; 514/300; 514/259; 514/260; 514/322; 514/252; 514/253; 514/316; 514/255; 514/247; 514/311; 514/226; 514/312; 514/313; 514/314; 514/269; 514/273; 514/274; 514/275

[58] Field of Search ............... 546/118, 187, 193, 199, 546/174, 171, 172, 153; 544/238, 333, 331, 328, 295, 296, 316, 284, 353, 405, 224, 55, 298; 424/267, 263, 250, 251, 258; 514/272, 300, 322, 316, 311, 312, 313, 314, 269, 273, 274, 275, 259, 260, 252, 253, 255, 247

[56] References Cited

U.S. PATENT DOCUMENTS 4,219,559 8/1980 Janssens et al. .................... 546/199

OTHER PUBLICATIONS

Wauwe et al., Chem. Abst. 95: 73643h.

*Primary Examiner*—Jane T. Fan
*Attorney, Agent, or Firm*—Geoffrey G. Dellenbaugh

[57] ABSTRACT

Novel N-(bicyclic heterocyclyl)-4-piperidinamines having antihistaminic and serotonin-antagonistic properties which are useful in the treatment of allergic diseases.

15 Claims, No Drawings

N-(BICYCLIC HETEROCYCLYL)-4-PIPERIDINAMINES

CROSS-REFERENCE TO RELATED APPLICATIONS

This is a continuation-in-part of our co-pending application Ser. No. 397,626 filed July 12, 1982, now abandoned.

BACKGROUND OF THE INVENTION

In U.S. Pat. No. 4,219,559 there are described a number of N-heterocyclyl-4-piperidinamines having the formula

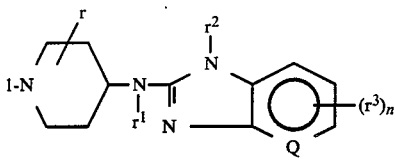

which compounds are useful as antihistaminic agents.

The compounds of the present invention differ from the prior art compounds essentially by the nature of the 1-piperidinyl substituent and by the fact that the compounds of the present invention are not only potent histamine-antagonists but also potent serotonin-antagonists.

DESCRIPTION OF THE PREFERRED EMBODIMENTS

This invention is concerned with novel N-heterocyclyl-4-piperidinamines which may structurally be represented by the formula

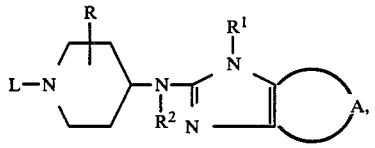 (I)

the pharmaceutically acceptable acid addition salts and the stereochemically isomeric forms thereof, wherein:

A is a bivalent radical having the formula

—CH=CH—CH=CH—  (a),

—N=CH—CH=CH—  (b),

—CH=N—CH=CH—  (c),

—CH=CH—N=CH—  (d), or

—CH=CH—CH=N—  (e), wherein one or two hydrogen atoms in said radicals (a)—(e) may, each independently from each other, be replaced by halo, lower alkyl, lower alkyloxy, trifluoromethyl or hydroxy;

R is a member selected from the group consisting of hydrogen and lower alkyl;

$R^1$ is a member selected from the group consisting of hydrogen, alkyl, cycloalkyl, $Ar^1$ and lower alkyl substituted with one or two $Ar^1$ radicals;

$R^2$ is a member selected from the group consisting of hydrogen, lower alkyl, cycloalkyl, (lower alkyl)—CO— and $Ar^2$-lower alkyl;

L is a member selected from the group consisting of a radical of formula

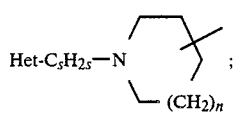 (f)

a radical of formula

Het—$C_sH_{2s}$—Y—Alk—  (g); and a radical of formula

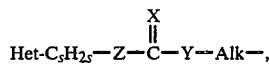 (h)

wherein n is 0 or the integer 1 or 2;
s is 0 or an integer of from 1 to 6 inclusive;
Alk is lower alkanediyl;
Y is O, S, $NR^3$ or a direct bond;
X is O, S, CH—$NO_2$ or $NR^4$;
Z is O, S, $NR^5$ or a direct bond; and
Het is an optionally substituted 6-membered heterocyclic ring having at least one nitrogen atom and being optionally condensed with an optionally substituted benzene ring, said Het being connected to $C_sH_{2s}$ on a carbon atom;
said $R^3$ being hydrogen, lower alkyl, ($Ar^2$)lower alkyl, 2-lower alkyloxy-1,2-dioxoethyl or a radical of formula —C(=X)—$R^6$, $R^6$ being hydrogen, lower alkyl, $Ar^2$, $Ar^2$-lower alkyl, lower alkyloxy, $Ar^2$-lower alkyloxy, mono- or di(lower alkyl)amino, $Ar^2$-lower alkylamino or $Ar^2$-lower alkyl(lower alkyl)amino;
said $R^4$ being hydrogen, lower alkyl, cyano, nitro, $Ar^2$-sulfonyl, lower alkylsulfonyl, lower alkylcarbonyl or $Ar^2$-carbonyl; and
said $R^5$ being hydrogen or lower alkyl;
provided that Het is other than pyridinyl or mono- or di(lower alkyloxy)pyridinyl where L is a radical (g) wherein Y is $NR^3$ or where L is a radical (h) wherein X is O and Z is $NR^5$ or a direct bond;
wherein $Ar^1$ is a member selected from the group consisting of phenyl, being optionally substituted with up to three substituents each independently selected from the group consisting of halo, hydroxy, nitro, cyano, trifluoromethyl, lower alkyl, lower alkyloxy, lower alkylthio, mercapto, amino, mono- and di(lower alkyl)amino, carboxyl, lower alkyloxycarbonyl and (lower alkyl)—CO—; thienyl; halothienyl; furanyl; lower alkyl substituted furanyl; pyridinyl; pyrazinyl; thiazolyl and imidazolyl optionally substituted by lower alkyl; and wherein $Ar^2$ is a member selected from the group consisting of phenyl being optionally substituted with up to three substituents each independently selected from the group consisting of halo, hydroxy, nitro, cyano, trifluoromethyl, lower alkyl, lower alkyloxy, lower alkylthio, mercapto, amino, mono- and di(lower alkyl)amino, carboxyl, lower alkyloxycarbonyl and (lower alkyl)—CO.

As used in the foregoing definitions the term halo is generic to fluoro, chloro, bromo and iodo; the term "lower alkyl" is meant to include straight and branch chained saturated hydrocarbon radicals having from 1 to 6 carbon atoms such as, for example, methyl, ethyl, 1-methylethyl, 1,1-dimethylethyl, propyl, 2-methylpropyl, butyl, pentyl, hexyl and the like; "alkyl" is meant to include lower alkyl radicals, as defined hereinabove, and the higher homologs thereof having from 7 to 10 carbon atoms; the term "cycloalkyl" is generic to cyclopropyl, cyclobutyl, cyclopentyl and cyclohexyl; and "lower alkanediyl" is meant to include bivalent straight or branch chained alkanediyl radicals having from 1 to 6 carbon atoms.

The compounds of formula (I) wherein Het is a heterocycle which is substituted with a hydroxy radical may contain in their structure a keto-enol system or a vinylog system thereof and consequently these compounds may be present in their keto form as well as their enol form.

Preferred compounds within the invention are those wherein Het is a member selected from the group consisting of a pyridinyl radical which is optionally substituted with one or two substituents each independently selected from the group consisting of halo, amino, nitro, cyano, aminocarbonyl, lower alkyl, lower alkyloxy, lower alkylthio, lower alkyloxycarbonyl, hydroxy, lower alkylcarbonyloxy, $Ar^2$-lower alkyl and carboxyl; a pyridinyloxide radical optionally substituted with nitro, a quinolinyl radical which is optionally substituted with a lower alkyl radical; a pyrimidinyl radical which is optionally substituted with one or two substituents each independently selected from the group consisting of halo, amino, hydroxy, lower alkyl, lower alkyloxy, lower alkylthio and ($Ar^2$)-lower alkyl; a quinazolinyl radical which is optionally substituted with a hydroxy radical or a lower alkyl radical; a pyridazinyl radical which is optionally substituted with a lower alkyl radical or a halo radical; a quinoxalinyl radical which is optionally substituted with a lower alkyl radical; a pyrazinyl radical which is optionally substituted with a halo radical, an amino radical or a lower alkyl radical; a phthalazinyl radical which is optionally substituted by a halo radical; and a 5,6-dihydro-4$\underline{H}$-1,3-thiazin-2-yl radical.

Particularly preferred compounds are those wherein L is a radical (g) or (h) wherein Het is as described hereinabove for the preferred compounds.

More particularly preferred compounds are those wherein L is a radical (g) or (h) wherein Het is other than an optionally substituted pyridinyl radical.

The most preferred compounds are selected from the group consisting of 1-[(4-fluorophenyl)methyl]-N-[1-[2-[(2-pyrimidinyl)amino]ethyl]-4-piperidinyl]-1$\underline{H}$-benzimidazol-2-amine and the pharmaceutically acceptable acid-addition salts thereof.

The compounds of formula (I) can generally be prepared by reacting an intermediate of formula (II) with a piperidine of formula (III) following art-known alkylating procedures.

Het—Q$_1$ +

(II)

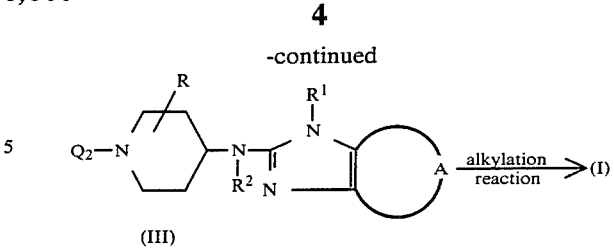

(III)

In (II) and (III) Het, R, R$^1$, R$^2$ and A are as previously described and Q$_1$ and Q$_2$ are selected so that in combination with Het a bivalent radical of formula (f), (g) or (h) is formed during the alkylation reaction, said (f), (g) and (h) having the previously described meaning.

For example, the compounds of formula (I) can generally be prepared by N-alkylating a piperidine of formula (III) wherein Q$_2$ is hydrogen, said piperidine being represented by the formula (III-a), with a reagent of formula (II) having the general formula L-W, (II-a).

L—W +

(II-a)

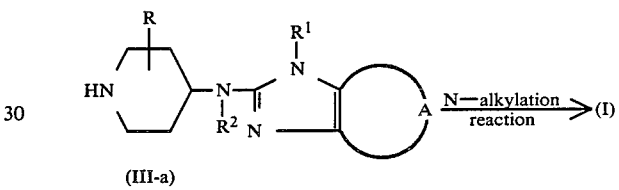

(III-a)

In (II-a) W represents an appropriate reactive leaving group such as, for example, halo, e.g., chloro, bromo or iodo, or a sulfonyloxy group, e.g. methylsulfonyloxy or 4-methylphenylsulfonyloxy.

Additionally, the compounds of formula (I) wherein L is a radical of formula (f), a radical of formula (g) wherein Y is other than a direct bond, Y', or a radical of formula (h) wherein Z is other than a direct bond, Z', said compounds being represented by the formulae (I-a-1), respectively (I-a-2) and (I-a-3), can be prepared by alkylating a piperidine of formula (III-b) with a reagent of formula (II-b).

Het—C$_s$H$_{2s}$—W' +

(II-b)

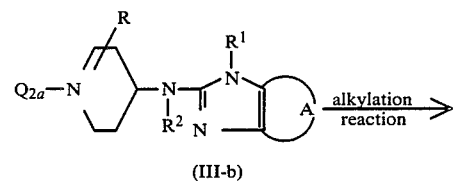

(III-b)

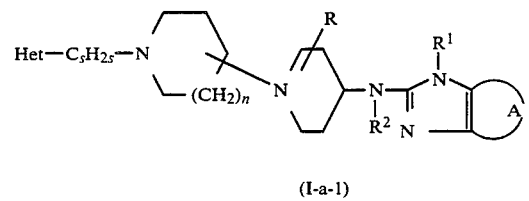

(I-a-1)

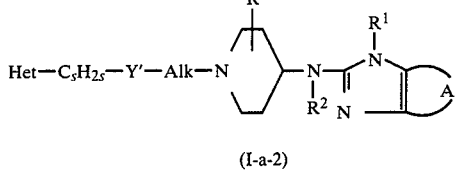

(I-a-2)

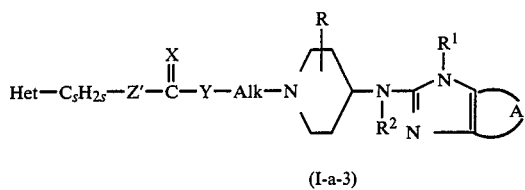

(I-a-3)

In (III-b) $Q_{2a}$ is a radical of formula

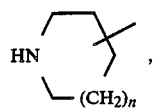

respectively a radical of formula HY'—Alk— or

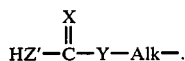

In (II-b) W' has the previously defined meaning of W and, where s is 0, it may also represent a lower alkyloxy or lower alkylthio group.

The compounds of formula (I-a-2) may also be prepared by alkylating a piperidine of formula (III) wherein $Q_2$ is a radical of formula —Alk—W, said piperidine being represented by the formula (III-c), with a reagent of formula (II) wherein $Q_1$ is a radical of formula —$C_sH_{2s}$—Y'H, said reagent being represented by the formula (II-c).

Het—$C_sH_{2s}$—Y'H +

(II-c)

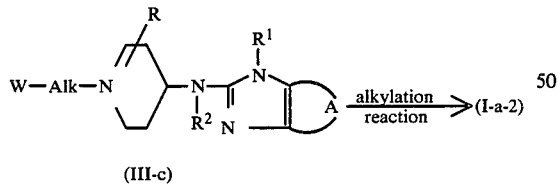

The compounds of formula (I) wherein L is a radical of formula Het—$C_sH_{2s}$—Z—C(=X)—Y'—Alk, said compounds being represented by the formula (I-a-4), may also be prepared by N-alkylating a piperidine of formula (III-c) with a reagent of formula (II) wherein $Q_2$ is a radical of formula —$C_sH_{2s}$—Z—C(=X)—Y'H, said reagent being represented by the formula (II-d).

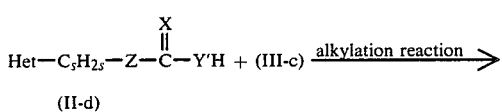

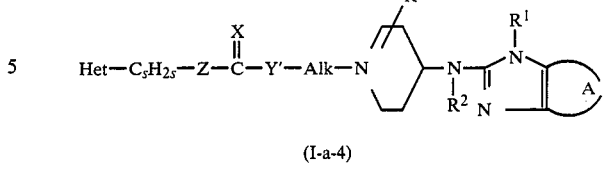

(I-a-4)

The alkylation reactions are conveniently conducted in an inert organic solvent such as, for example, an aromatic hydrocarbon, e.g., benzene, methylbenzene, dimethylbenzene, and the like; a lower alkanol, e.g., methanol, ethanol, 1-butanol and the like; a ketone, e.g., 2-propanone, 4-methyl-2-pentanone and the like; and ether, e.g., 1,4-dioxane, 1,1'-oxybisethane, tetrahydrofuran and the like; N,N-dimethylformamide (DMF); N,N-dimethylacetamide (DMA); nitrobenzene; 1-methyl-2-pyrrolidinone; and the like. The addition of an appropriate base such as, for example, an alkali metal carbonate or hydrogen carbonate, sodium hydride or an organic base such as, for example, N,N-diethylethanamine or N-(1-methylethyl)-2-propanamine may be utilized to pick up the acid which is liberated during the course of the reaction. In some circumstances the addition of an iodide salt, preferably an alkali metal iodide, is appropriate. Somewhat elevated temperatures may enhance the rate of the reaction.

The compounds of formula (I) wherein L is a radical of formula (h) wherein Z is Z', Y is NH and X is O or S, said X being represented by X' and said compounds by the formula (I-b-1), can generally be prepared by reacting an isocyanate or isothiocyanate of formula (V) with a reagent of formula (IV).

Het—$C_sH_{2s}$—Z'H +

(IV)

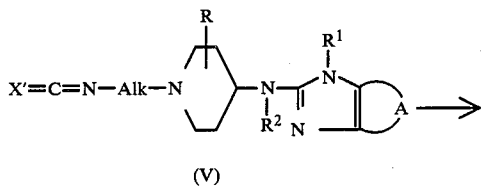

(V)

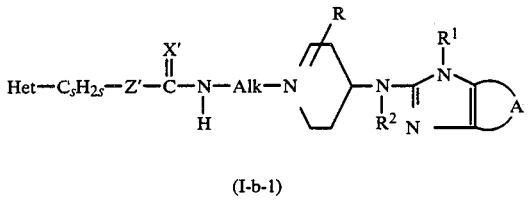

(I-b-1)

The compounds of formula (I) wherein L is a radical of formula (h) wherein Z is NH, Y is Y' and X is X', said compounds being represented by the formula (I-b-2), can be prepared by reacting an isocyanate or isothiocyanate of formula (VI) with a piperidine of formula (VII).

Het—$C_sH_{2s}$—N=C=X' +

(VI)

-continued

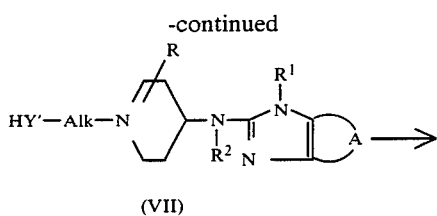

(VII)

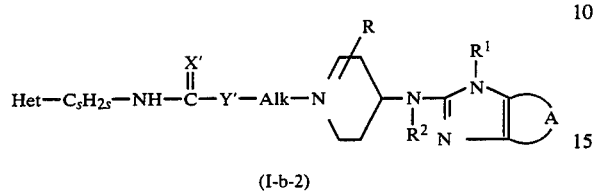

(I-b-2)

The reaction of (IV) with (V) and (VI) with (VII) is generally conducted in a suitable reaction-inert solvent such as, for example, an ether, e.g., tetrahydrofuran and the like. Elevated temperatures may be suitable to enhance the rate of the reaction.

The compounds of formula (I) wherein L is a radical of formula (h) wherein Z is a direct bond and X is X', said compounds being represented by the formula (I-c), may be prepared by reacting a piperidine of formula (VII) with a reagent of formula (VIII).

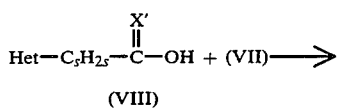

(VIII)

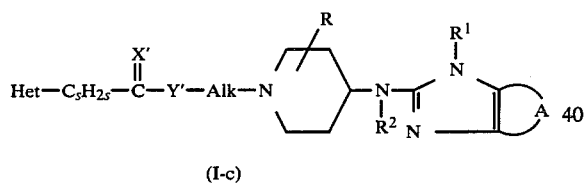

(I-c)

The reaction of (VII) and (VIII) may generally be conducted following art-known esterification- or amidation reaction-procedures, e.g., by converting the carboxylic acid function into a reactive derivative, e.g., an anhydride or a carboxylic halide function, and subsequently reacting this reactive derivative with a reagent of formula (VII). A suitable reaction is, for example, by stirring (VIII) with 2-quinolinecarboxylic acid in a suitable solvent in the presence of N,N-diethylethanamine and converting the intermediately formed reactive product into the desired ester or amide.

The compounds of formula (I) wherein L is a radical of formula (g) wherein Y is a direct bond and s is 0, said compounds being represented by the formula (I-d), may also be prepared by reacting an alkenylene of formula (IX) with a piperidine of formula (III-a) by stirring and, if desired, heating the reactants together.

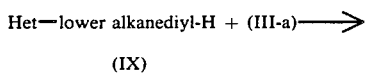

(IX)

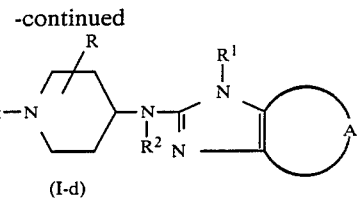

(I-d)

The compounds of formula (I) can also be prepared by the cyclodesulfurization reaction of an appropriate thiourea derivative of the formula

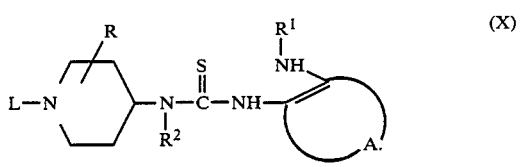

(X)

Said cyclodesulfurization reaction may be carried out by the reaction of (X) with an appropriate alkyl halide, preferably iodomethane in an appropriate reaction-inert organic solvent, e.g., a lower alkanol such as methanol, ethanol, 2-propanol and the like. Otherwise, the cyclodesulfurization reaction may be carried out by the reaction of (X) with an appropriate metal oxide or salt in an appropriate solvent according to art-known procedures.

For example, the compounds of formula (I) can easily be prepared by the reaction of (IV) with an appropriate Hg(II) or Pb(II) oxide or salt, such as, for example HgO, HgCl$_2$, Hg(OAc)$_2$, PbO or Pb(OAc)$_2$. In certain instances it may be appropriate to supplement the reaction mixture with a small amount of sulfur. Even so methanediimines, especially N,N'-methanetetraylbis[cyclohexanamine] may be used as cyclodesulfurizing agents. Suitable reaction-inert organic solvents that may advantageously be employed include lower alkanols, e.g., methanol, ethanol, 2-propanol and the like; halogenated hydrocarbons, e.g., dichloromethane and trichloromethane; ethers, e.g. tetrahydrofuran, 2,2'-oxybispropane and the like; and mixtures of such solvents.

The compounds of formula (I) can also be converted into each other following art-known procedures of functional grouptransformation. Some examples will be cited hereinafter.

The compounds of formula (I) having a nitro substituent can be converted into their corresponding amines by stirring and, if desired, heating the starting nitro-compounds in a hydrogen-containing medium in the presence of a suitable amount of an appropriate catalyst such as, for example, platinum-on-charcoal, palladium-on-charcoal, Raney-nickel and the like catalysts. Suitable solvents are, for example, alcohols, e.g., methanol, ethanol and the like.

Halo atoms substituted on aryl groups may be replaced by hydrogen following art-known hydrogenolysis procedures, i.e. by stirring and, if desired, heating the starting compounds in a suitable solvent under hydrogen atmosphere in the presence of an appropriate catalyst, e.g., palladium-on-charcoal and the like catalysts. Said halo atoms may also be replaced by a lower alkyloxy or a lower alkylthio substituent by reacting the starting halo-compound with an appropriate alcohol or thioalcohol or, preferably, an alkali- or earth alkaline metal salt or an appropriate alcohol or thioalcohol in a suitable solvent.

The compounds of formula (I) wherein L is a radical (g) wherein Y is NH can be converted into a compound of formula (I) wherein L is a radical (g) wherein Y is N—CO(lower alkyl) or N—CO(Ar²) by reacting the starting amine with an appropriate carboxylic acid or a derivative thereof such as, for example, an acid halide, an acid anhydride and the like.

In all of the foregoing and in the following preparations, the reaction products may be isolated from the reaction mixture and, if necessary, further purified according to methodologies generally known in the art.

The compounds of formula (I) have basic properties and, consequently, they may be converted to their therapeutically active non-toxic acid addition salt forms by treatment with appropriate acids, such as, for example, inorganic acids, such as hydrohalic acid, e.g. hydrochloric, hydrobromic and the like, and sulfuric acid, nitric acid, phosphoric acid and the like; or organic acids, such as, for example, acetic, propanoic, hydroxyacetic, 2-hydroxypropanoic, 2-oxopropanoic, propanedioic, butanedioic, (Z)-2-butenedioic, (E)-2-butenedioic, 2-hydroxybutanedioic, 2,3-dihydroxybutanedioic, 2-hydroxy-1,2,3-propanetricarboxylic, methanesulfonic, ethanesulfonic, benzenesulfonic, 4-methylbenzenesulfonic, cyclohexanesulfamic, 2-hydroxybenzoic, 4-amino-2-hydroxybenzoic and the like acids.

Conversely the salt form can be converted by treatment with alkali into the free base form.

A number of intermediates and starting materials in the foregoing preparations are known compounds which may be prepared according to art-known methodologies of preparing said or similar compounds and some intermediates are new. A number of such preparation methods will be described hereinafter in more detail.

The intermediates of formula (III-a) can conveniently be prepared starting from a thiourea derivative of formula

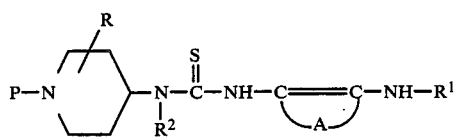

wherein P is an appropriate protective group such as, for example, lower alkyloxycarbonyl, Ar²—CH₂—O—CO—, Ar²—CH₂— and the like, by a cyclodesulfurization reaction following the same procedure as described hereinabove for the preparation of (I) starting from (X) and, subsequently, eliminating the protective group P in the thus obtained intermediate of formula

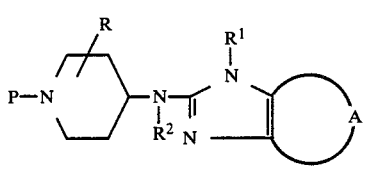

The elimination of the protective group P in (XII) may generally be carried out following art-known procedures such as, for example, by hydrolysis in alkaline or acidic aqueous medium.

The intermediates of formula (III-b) and (III-c) may be derived from the corresponding intermediates of formula (III-a) by reacting the latter with a suitable reagent following art-known N-alkylating procedures.

For example, intermediates of formula (III-b) wherein Q₂ₐ represents a radical of formula H₂N—CH₂—Alk′—, (III-b-1), can also be prepared by reacting an intermediate of formula (III-a) with a nitrile of formula (XIII) following art-known N-alkylating procedures and subsequently converting the thus obtained nitrile (XIV) into the corresponding amine (III-b-1) following art-known nitrile to amine reducing procedures, e.g., by catalytically hydrogenating procedures and the like.

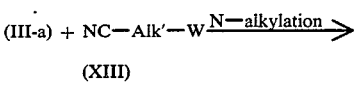

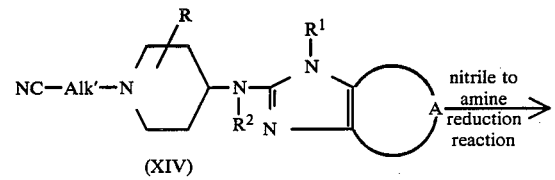

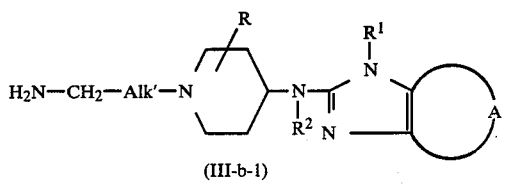

In (XIII), (XIV) and (III-b-1) Alk′ has the same meaning as Alk provided that one methylene function is missing.

The intermediates of formula (III-b) wherein Q₂ₐ represents a radical of formula HY′—CH₂—CH₂—, (III-b-2), may also be prepared by the reaction of (III-a) with a reagent of formula (XV) by stirring and, if desired, heating the reactants together in a suitable solvent.

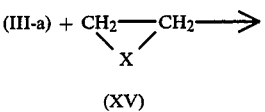

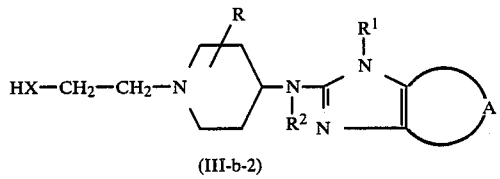

The intermediates of formula (III-b) wherein Q₂ₐ is a radical of formula HX—Alk—, (III-d), may be converted into an intermediate of formula (III-c) by converting the function XH into an appropriate leaving group, e.g., where X is O, by converting a hydroxy function into a chloro atom, with thionyl chloride, phosphoryl chloride and the like.

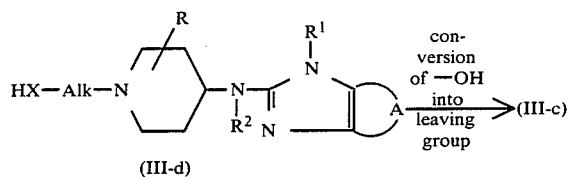

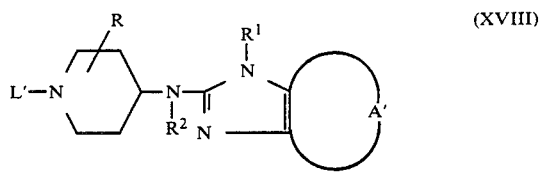

The intermediates of formula (III-b-1) may also be derived from an appropriate corresponding carbonyl-oxidated form by reacting said carbonyl-oxidated form with hydroxylamine and reducing the thus obtained oxime following art-known methods, e.g., catalytic hydrogenation and the like reducing methods.

During one of the reactions the intermediates wherein $R^1$ and/or $R^2$ and/or $R^3$ and/or $R^4$ is hydrogen may be converted into the corresponding intermediates wherein $R^1$ and/or $R^2$ and/or $R^3$ and/or $R^4$ is other than hydrogen following art-known N-alkylating, N-acylating or reductive N-alkylating procedures.

The intermediates of formula (XI) may be prepared by reacting a piperidine of formula (XVI-a) or (XVI-b) with an aromatic reagent of formula (XVII-a) or (XVII-b).

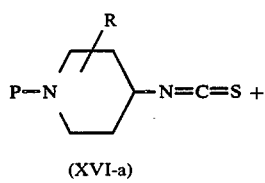

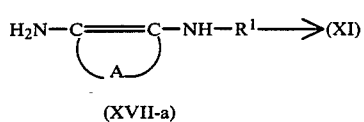

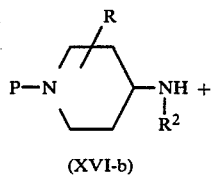

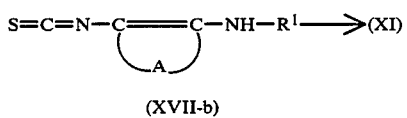

The intermediates of formulae (III-b) and (XIV) wherein A is a radical having the formula (c), (d) or (e), (III-b-2), respectively (XIV-a) are new and as intermediates as well as antihistaminic agents and serotonin-antagonists these 3H-imidazo[4,5-c]pyridin-2-amines, 1H-imidazo[4,5-b]pyridin-2-amines and 1H-imidazo[4,5-c]pyridin-2-amines of formulae (III-b) and (XIV) constitute an additional purpose of the present invention.

The compounds of formula (I) and the intermediates of formula (III-b-2) and (XIV-a) wherein A is a radical of formula —CH=N—CH=CH—, —CH=CH—N=CH— or —CH=CH—CH=N—, N being attached to the carbon atom in 4-position of the imidazole ring, said A being represented by A' and said intermediates by the formula and the pharmaceutically acceptable acid addition salts thereof, wherein L' is a radical of formula —Alk'—CN, —Alk—Y'H,

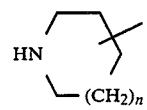

or —Alk—Y—C(=X)—Z'H are useful as anti-allergic agents.

From formula (I) and (XVIII) it is evident that the compounds of this invention may have several asymmetric carbon atoms in their structure. Each of these chiral centers may be present in a R- and a S-configuration, this R- and S-notation being in correspondence with the rules described by R. S. Cahn, C. Ingold and V. Prelog in Angew. Chem., Int. Ed. Engl., 5, 385, 511 (1966).

Pure stereochemically isomeric forms of the compounds of formula (I) and (XVIII) may be obtained by the application of art-known procedures. Diastereoisomers may be separated by physical separation methods such as selective crystallization and chromatographic techniques, e.g., counter current distribution, and enantiomers may be separated from each other by the selective crystallization of their diastereomeric salts with optically active acids.

Pure stereochemically isomeric forms may also be derived from the corresponding pure stereochemically isomeric forms of the appropriate starting materials, provided that the reaction occurs stereospecifically.

It is evident that the cis and trans diastereomeric racemates may be further resolved into their optical isomers, cis(+), cis(−), trans(+) and trans(−) by the application of methodologies known to those skilled in the art.

Stereochemically isomeric forms of the compounds of formula (I) and the intermediates of formula (XVIII) are naturally intended to be embraced within the scope of the invention.

The useful antihistaminic properties of the compounds of formula (I) and of the intermediates of formula (XVIII) are demonstrated in the following test procedure.

Protection of rats from compound 48/80-induced lethality

Compound 48/80, a mixture of oligomers obtained by condensation of 4-methoxy-N-methylbenzeneethanamine and formaldehyde has been described as a potent histamine releasing agent (Int. Arch. Allergy, 13, 336 (1958)). The protection from compound 48/80-induced lethal circulatory collapse appears to be a simple way of evaluating quantitatively the antihistaminic activity of test compounds. Male rats of an inbred Wistar strain, weighing 240–260 g were used in the experiment. After overnight starvation the rats were transferred to conditioned laboratories (temp.=21±1° C., relative humidity—65±5%).

The rats were treated subcutaneously or orally with a test compound or with the solvent (NaCl solution, 0.9%). One hour after treatment there was injected intravenously compound 48/80, freshly dissolved in water, at a dose of 0.5 mg/kg (0.2 ml/100 g of body weight). In control experiments, wherein 250 solvent-treated animals were injected with the standard dose of compound 48/80, not more than 2.8% of the animals survived after 4 hours. Survival after 4 hours is therefore considered to be a safe criterion of a protective effect of drug administration.

The $ED_{50}$-values of the compounds of formula (I) and the intermediates of formula (XVIII) are listed in the first column of table 1 and table 2. Said $ED_{50}$-values are the values in mg/kg body weight at which the tested compounds protect 50% of the tested animals against compound 48/80-induced lethality.

The compounds of formula (I), the intermediates of formula (XVIII) and the pharmaceutically acceptable acid addition salts thereof are also potent serotonin-antagonists.

The potency of the subject compounds as serotonin-antagonists is clearly evidenced by the results obtained in the following tests wherein the antagonistic activity of the subject compounds on the effect of serotonin is examined.

Antagonistic activity on the effects of serotonin in the gastric lesion test

A. Lesions induced by compound 48/80

Compound 48/80 (a mixture of oligomers obtained by condensation of 4-methoxy-N-methylbenzeneethanamine and formaldehyde) is a potent releaser of vasoactive amines from endogenous stores such as, for example, histamine and serotonin. Rats injected with compound 48/80 exhibit consistent changes of blood flow in different vascular beds: cyanosis of the ears and the extremities are prominent within five minutes after injection of the compound; the rats die from shock within 30 minutes. The shock, followed by dead, can be avoided if the rats are pretreated with a classical H 1-antagonist.

However the stimulatory effects on gastric secretion are not suppressed so that rats treated with compound 48/80 and protected from shock by an H 1-antagonist may exhibit all signs of intensive gastric gland activity; gross autopsy shows distended stomachs with abnormal contents and rough bright red patches all over the mucosa, corresponding to areas of disintegrated glands. A number of known serotonin-antagonists such as, for example, methysergide, cyproheptadine; cinanserin, mianserin, pipamperone, spiperone, pizotifen and metergoline, prevent completely the cyanosis of ears and extremities as well as the lesions in the glandular area of the stomach and the abnormal gastric distension.

B. Method

Male rats of a Wistar inbred strain, weighing 220–250 g, were starved overnight, water being available ad libitum. The test compounds were administered orally as a solution or as a suspension in aqueous medium. A control rat and a "blank" rat received the test compound. One hour later 5-[4-(diphenylmethyl)-1-piperazinylmethyl]-1-methyl-1H-benzimidazole-2-methanol was administered subcutaneously to all rats at the dose of 2.5 mg/kg. Two hours after the oral or subcutaneous administration of the test compound, the compound 48/80 (freshly solved in water at a concentration of 0.25 mg/ml) was injected intravenously into all rats (dose: 1 mg/kg) except the "blank" rats.

Four hours after the intravenous injection of compound 48/80, the rats were decapitated and the stomachs were removed. Subsequently the stomachs were inspected for distension and contents (blood, fluid, food) and thoroughly rinsed. The macroscopic lesions were scored from 0 to ++, 0 corresponding to complete absence of visible lesions and the highest score corresponding to reddish rough patches covering more than half the glandular area.

The second column of Tables 1 and 2 shows for a number of compounds of formula (I) and the intermediates of formula (XVIII) the doses (in mg/kg body weight) at which the distension of the stomach as well as the lesions in the glandular area of the stomach are completely absent in 50% of the test rats ($ED_{50}$-value).

The columns in Tables 1 and 2 with heading "N" illustrate the absence or the presence of N in the aromatic ring and the place of N in the said ring.

In the tables 1 and 2 "b" has the meaning of branch chained hydrocarbon radicals.

The compounds listed in Tables 1 and 2 are not given for the purpose of limiting the invention thereto but only to exemplify the useful pharmacological activities of all the compounds within the scope of formula (I) and of all the intermediates within the scope of formula (XVIII).

TABLE 1

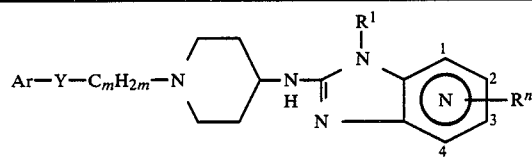

| Y | m | Ar | $R^1$ | $R^n$ | N | base or salt form | Column 1 compound 48/80 lethality test in rats-$ED_{50}$ in mg/kg body weight | Column 2 gastric lesion test $ED_{50}$ in mg/kg body weight |
|---|---|---|---|---|---|---|---|---|
| NH | 2 | 3-$NH_2$—2-pyridinyl | 4-F—$C_6H_4CH_2$ | H | — | 3HCl | 0.08 | 0.31 |
| NH | 2 | 3-$NH_2CO$—2-pyridinyl | 4-F—$C_6H_4CH_2$ | H | — | base | 0.08 | 0.16 |
| NH | 2 | 5-Br—2-pyridinyl | 4-F—$C_6H_4CH_2$ | H | — | base | 0.31 | 2.5 |
| NH | 2 | 3-Cl—2-pyridinyl | 4-F—$C_6H_4CH_2$ | H | — | base | 0.16 | 0.31 |
| NH | 2 | 5-$NO_2$—2-pyridinyl | 4-F—$C_6H_4CH_2$ | H | — | base | 0.31 | 2.5 |
| NH | 2 | 5-$NH_2CO$—2-pyridinyl | 4-F—$C_6H_4CH_2$ | H | — | base | 0.04 | 0.08 |
| NH | 2 | 3-Cl—2-pyridinyl | 4-F—$C_6H_4CH_2$ | H | 1 | base | 0.08 | 0.31 |

TABLE 1-continued

| | | | | | | | Column 1 compound 48/80 lethality test in rats-ED$_{50}$ in mg/kg body weight | Column 2 gastric lesion test ED$_{50}$ in mg/kg body weight |
|---|---|---|---|---|---|---|---|---|
| NH | 2 | 3-NH$_2$CO—2-pyridinyl | 4-F—C$_6$H$_4$CH$_2$ | H | 1 | base | 0.04 | 0.04 |
| NH | 2 | 5-NO$_2$, 6-NH$_2$—2-pyridinyl | 4-F—C$_6$H$_4$CH$_2$ | H | — | base | 0.31 | 2.5 |
| NH | 2 | 3-NH$_2$CO—2-pyridinyl | 2-furanylCH$_2$ | H | — | base | 0.04 | 0.63 |
| O | 2 | 5-Br—2-pyridinyl | 2-furanylCH$_2$ | H | — | base | 0.31 | — |
| NH | 2 | 4-NO$_2$—3-pyridinyl, N→O | 4-F—C$_6$H$_4$CH$_2$ | H | — | base | 0.04 | 1.25 |
| NH | 2 | 2-quinolinyl | 4-F—C$_6$H$_4$CH$_2$ | H | — | base | 0.31 | — |
| O | 2 | 2-quinolinyl | 4-F—C$_6$H$_4$CH$_2$ | H | — | base | 1.25 | 2.5 |
| NH | 2 | 2-pyrimidinyl | 4-F—C$_6$H$_4$CH$_2$ | H | — | base | 0.16 | 0.63 |
| NH | 4 | 2-pyrimidinyl | 4-F—C$_6$H$_4$CH$_2$ | H | — | base | 0.16 | 2.5 |
| NH | 3 | 2-pyrimidinyl | 4-F—C$_6$H$_4$CH$_2$ | H | — | base | 0.16 | — |
| NH | 2 | 2-pyrimidinyl | 2-furanylCH$_2$ | H | — | base | 0.16 | 0.04 |
| NH | 2 | 4-Cl, 6-CH$_3$—2-pyrimidinyl | 4-F—C$_6$H$_4$CH$_2$ | H | — | base | 0.63 | — |
| NH | 3b | 2-pyrimidinyl | 4-F—C$_6$H$_4$CH$_2$ | H | — | base | 0.63 | 0.63 |
| NBz | 2 | 2-pyrimidinyl | 4-F—C$_6$H$_4$CH$_2$ | H | — | base | 0.63 | 0.63 |
| NMe | 2 | 2-pyrimidinyl | 4-F—C$_6$H$_4$CH$_2$ | H | — | base | 0.08 | 0.63 |
| NAc | 2 | 2-pyrimidinyl | 4-F—C$_6$H$_4$CH$_2$ | H | — | 2(E)-2-butenedioate | 0.04 | 0.63 |
| NH | 2 | 4-n.C$_3$H$_7$, 6-OH—2-pyrimidinyl | 4-F—C$_6$H$_4$CH$_2$ | H | — | base | 0.31 | 2.5 |
| NH | 2 | 4-OH—2-pyrimidinyl | 4-F—C$_6$H$_4$CH$_2$ | H | — | base | 0.08 | 0.63 |
| NH | 2 | 6-Bz, 4-OH—2-pyrimidinyl | 4-F—C$_6$H$_4$CH$_2$ | H | — | base | 0.63 | — |
| NH | 2 | 6-Me, 4-OH—2-pyrimidinyl | 4-F—C$_6$H$_4$CH$_2$ | H | — | H$_2$O | 0.16 | 0.63 |
| NH | 2 | 2-pyrimidinyl | 4-F—C$_6$H$_4$CH$_2$ | H | 4 | base | 0.02 | 0.16 |
| NCPh ‖ O | 2 | 2-pyrimidinyl | 4-F—C$_6$H$_4$CH$_2$ | H | — | 2(E)-2-butenedioate | 0.08 | 0.63 |
| NH | 2 | 2-pyrimidinyl | 4-F—C$_6$H$_4$CH$_2$ | H | 3 | base | 0.08 | — |
| NH | 2 | 2-pyrimidinyl | 2-pyridinylCH$_2$ | H | — | base | 0.04 | 0.63 |
| NH | 2 | 2-pyrimidinyl | 4-F—C$_6$H$_4$CH$_2$ | 2(and 3)F | — | base | 0.04 | 0.08 |
| NH | 2 | 2-pyrimidinyl | 3-pyridinylCH$_2$ | H | — | base | 1.25 | — |
| NH | 2 | 2-pyrimidinyl | 2-pyrazinylCH$_2$ | H | — | base | 0.01 | 0.63 |
| NH | 2 | 2-pyrimidinyl | 4-F—C$_6$H$_4$CH$_2$ | H | 1 | base | 0.04 | 0.08 |
| NH | 2 | 2-pyrimidinyl | 2-furanylCH$_2$ | H | 1 | base | 0.04 | 0.63 |
| NH | 2 | 2-pyrimidinyl | 4-F—C$_6$H$_4$CH$_2$ | H | 2 | 2(E)-butenedioate | 0.16 | — |
| NH | 2 | 2-pyrimidinyl | 2-thienylCH$_2$ | H | — | base | 0.02 | 2.5 |
| NH | 2 | 2-pyrimidinyl | 3-furanylCH$_2$ | H | — | base | 0.04 | 0.63 |
| NH | 2 | 2-pyrimidinyl | 5-CH$_3$—2-furanylCH$_2$ | H | — | base | 0.04 | 0.63 |
| S | 2 | 2-pyrimidinyl | 4-F—C$_6$H$_4$CH$_2$ | H | — | base | 0.16 | 0.16 |
| O | 2 | 2-pyrimidinyl | 4-F—C$_6$H$_4$CH$_2$ | H | — | base | 0.16 | 0.63 |
| O | 2 | 5-Br—2-pyridinyl | 4-F—C$_6$H$_4$CH$_2$ | H | — | base | 0.16 | — |
| O | 2 | 2-pyrimidinyl | 2-furanylCH$_2$ | H | — | 2(E)-butenedioate | 0.08 | 1.25 |
| NH | 2 | 2-pyrimidinyl | 2-pyridinylCH$_2$ | H | 1 | 1.½(E)-butenedioate | 0.04 | 2.5 |
| NH | 2 | 2-Cl—4-pyrimidinyl | 4-F—C$_6$H$_4$CH$_2$ | H | — | 2HCl.H$_2$O | 0.31 | 2.5 |
| NH | 2 | 2-Cl, 6-CH$_3$—4-pyrimidinyl | 4-F—C$_6$H$_4$CH$_2$ | H | — | base | 0.08 | 2.5 |
| NH | 2 | 6-Cl—4-pyrimidinyl | 4-F—C$_6$H$_4$CH$_2$ | H | — | 2HCl | 0.31 | — |
| NH | 2 | 4-pyrimidinyl | 4-F—C$_6$H$_4$CH$_2$ | H | — | ½H$_2$O | 0.08 | 1.25 |
| NH | 2 | 2,6-(NH$_2$)$_2$—4-pyrimidinyl | 4-F—C$_6$H$_4$CH$_2$ | H | — | H$_2$O | 0.08 | 0.16 |
| NH | 2 | 2-NH, 6-CH$_3$—4-pyrimidinyl | 4-F—C$_6$H$_4$CH$_2$ | H | — | H$_2$O | 0.31 | — |
| NH | 2 | 6-CH$_3$O—4-pyrimidinyl | 4-F—C$_6$H$_4$CH$_2$ | H | — | base | 0.16 | — |
| O | 2 | 2-CH$_3$S—4-pyrimidinyl | 4-F—C$_6$H$_4$CH$_2$ | H | — | base | 0.16 | 2.5 |
| NH | 2 | 4-OH, 5-(4-Cl—C$_6$H$_4$)CH$_2$—4-pyrimidinyl | 4-F—C$_6$H$_4$CH$_2$ | H | — | H$_2$O | 1.25 | 2.5 |
| NH | 2 | 4-OH—2-quinazolinyl | 4-F—C$_6$H$_4$CH$_2$ | H | — | base | 0.63 | 2.5 |
| S | 2 | 4-OH—2-quinazolinyl | 4-F—C$_6$H$_4$CH$_2$ | H | — | H$_2$O | 0.31 | 2.5 |
| NH | 2 | 4-quinazolinyl | 4-F—C$_6$H$_4$CH$_2$ | H | — | base | 0.08 | 2.5 |
| NH | 2 | 2-pyrazinyl | 4-F—C$_6$H$_4$CH$_2$ | H | — | base | 0.16 | 2.5 |
| NH | 2 | 3-CH$_3$—2-quinoxalinyl | 4-F—C$_6$H$_4$CH$_2$ | H | — | base | 1.25 | — |
| O | 2 | 3-CH$_3$—2-quinoxalinyl | 4-F—C$_6$H$_4$CH$_2$ | H | — | base | 2.5 | — |
| NH | 2 | 6-Cl—3-pyridazinyl | 4-F—C$_6$H$_4$CH$_2$ | H | — | base | 0.08 | 1.25 |

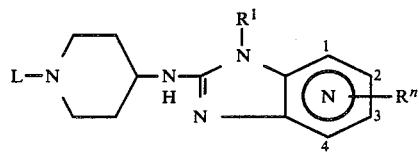

| | | | | | | Column 1 compound 48/80 lethality test in rats-ED$_{50}$ in mg/kg body weight | Column 2 gastric lesion test ED$_{50}$ in mg/kg body weight |
|---|---|---|---|---|---|---|---|
| L | | R$^1$ | R$^n$ | N | base or salt form | | |
| 1-(2-pyrimidinyl)-4-piperidinyl | | 4-F—C$_6$H$_4$CH$_2$ | H | — | base | 1.25 | — |

TABLE 1-continued

| | | | | | | |
|---|---|---|---|---|---|---|
| 1-(2-pyrimidinyl)-3-piperidinyl | 4-F—C₆H₄CH₂ | H | — | base | 1.25 | 2.5 |
| 1-(3-NO₂—2-pyridinyl)-4-piperidinyl | 4-F—C₆H₄CH₂ | H | — | 2H₂O | 0.63 | — |

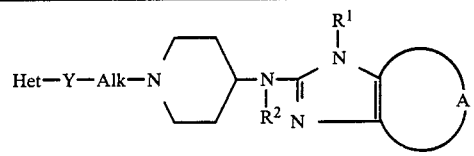

Het = 6-membered

| Het | Y | Alk | R¹ | R² | A | base or salt form | Column 1 compound 48/80 lethality test in rats ED₅₀ in mg/kg body weight | Column 2 gastric lesion test ED₅₀ in mg/kg body weight |
|---|---|---|---|---|---|---|---|---|
| 2-pyrazinyl | direct bond | (CH₂)₂ | 4-F—C₆H₄CH₂ | H | CH=CH—CH=CH | base | 0.31 | — |
| 2-pyridinylCH₂ | O | (CH₂)₂ | 4-F—C₆H₄CH₂ | H | CH=CH—CH=CH | 2(E)-butenedioate | 0.08 | 2.5 |
| 2-pyrimidinyl | NH | (CH₂)₂ | 4-thiazolylCH₂ | H | CH=CH—CH=CH | 2(E)-butenedioate | 0.02 | 0.08 |
| 2-pyrimidinyl | NH | (CH₂)₅ | 4-F—C₆H₄CH₂ | H | CH=CH—CH=CH | base | 0.31 | 0.08 |
| 2-pyrimidinyl | NH | (CH₂)₂ | C₆H₅CH₂ | H | CH=CH—CH=CH | base | 0.08 | 0.31 |
| 2-pyrimidinyl | NH | (CH₂)₂ | 4-CH₃—C₆H₄CH₂ | H | CH=CH—CH=CH | base | 0.16 | 0.63 |
| 2-pyrimidinyl | NH | (CH₂)₂ | 4-Cl—C₆H₄CH₂ | H | CH=CH—CH=CH | base | 0.16 | 2.5 |
| 2-pyrimidinyl | NH | (CH₂)₂ | 4-CH₃O—C₆H₄CH₂ | H | CH=CH—CH=CH | base | 0.31 | 2.5 |
| 5-Br—2-pyridinyl | NH | (CH₂)₂ | C₆H₅CH₂ | H | CH=CH—CH=CH | base | 0.31 | 2.5 |
| 2-pyrimidinyl | NH | (CH₂)₂ | 4-F—C₆H₄CH₂ | H | CH=CH—C(CH₃O)=CH | base | 1.25 | 2.5 |
| 5-Br—2-pyridinyl | NH | (CH₂)₂ | 4-CH₃—C₆H₄CH₂ | H | CH=CH—CH=CH | base | 0.02 | 0.08 |
| 2-pyrimidinyl | NH | (CH₂)₂ | 4-F—C₆H₄CH₂ | H | CH=CH—C(HO)=CH | base | 0.16 | 2.5 |
| 2-pyrimidinyl | NH | (CH₂)₂ | 4-OH—C₆H₄CH₂ | H | CH=CH—CH=CH | base | 2.5 | 2.5 |
| 5-NH₂, 6-Cl—4-pyrimidinyl | NH | (CH₂)₂ | 4-F—C₆H₄CH₂ | H | CH=CH—CH=CH | base | 0.16 | 1.25 |
| 5-NH₂—4-pyrimidinyl | NH | (CH₂)₂ | 4-F—C₆H₄CH₂ | H | CH=CH—CH=CH | base | 0.08 | 0.02 |
| 2-pyrimidinyl | NH | (CH₂)₂ | 4-F—C₆H₄CH₂ | H | CH=C(OCH₃)—CH=CH | base | 1.25 | 2.5 |
| 1-(2-pyridinyl) | 4-piperidinyl | (CH₂)₂ | 4-F—C₆H₄CH₂ | H | CH=CH—CH=CH | 1.½(E)-2-butenedioate.H₂O | 0.63 | 2.5 |
| 2-pyrimidinyl | NH | (CH₂)₂ | 4-F—C₆H₄CH₂ | CH₃ | CH=CH—CH=CH | base | 0.08 | 0.63 |
| 5-Cl—2-pyridinyl | NCH₃ | (CH₂)₂ | 4-F—C₆H₄CH₂ | H | CH=CH—CH=CH | base | 0.31 | 1.25 |
| 5-Cl—2-pyridinyl | NH | (CH₂)₃ | 4-F—C₆H₄CH₂ | H | CH=CH—CH=CH | 3HCl.H₂O | 0.63 | 2.5 |

| Het | —Z—C(=X)—Y | Alk | R¹ | A | base or salt form | Column 1 compound 48/80 lethality test in rats ED₅₀ in mg/kg body weight | Column 2 gastric lesion test ED₅₀ in mg/kg body weight |
|---|---|---|---|---|---|---|---|
| 3-pyridinyl | NH—CS—NH | (CH₂)₂ | 4-F—C₆H₄CH₂ | CH=CH—CH=CH | base | 0.63 | 0.63 |
| 2-pyridinyl | NH—CS—NH | (CH₂)₂ | 4-F—C₆H₄CH₂ | CH=CH—CH=CH | base | 0.63 | 0.63 |
| 3-NH₂—2-pyridinyl | NH—CS—NH | (CH₂)₂ | 4-F—C₆H₄CH₂ | CH=CH—CH=CH | base | 0.16 | 0.31 |
| 2-Cl—3-pyridinyl | CO—NH | (CH₂)₂ | 4-F—C₆H₄CH₂ | CH=CH—CH=CH | 2(E)-2-butenedioate.½H₂O | 0.16 | — |
| 6-Cl—3-pyridinyl | CO—NH | (CH₂)₂ | 4-F—C₆H₄CH₂ | CH=CH—CH=CH | 2(E)-2-butenedioate | 0.31 | 2.5 |
| 2-quinolinyl | CO—O | (CH₂)₂ | 4-F—C₆H₄CH₂ | CH=CH—CH=CH | 2(E)-2-butenedioate | 0.04 | 0.63 |
| 3-NH₂—2-pyrazinyl | CO—NH | (CH₂)₂ | 4-F—C₆H₄CH₂ | CH=CH—CH=CH | base | 0.04 | 0.16 |

TABLE 2

[Structure: L'—N(piperidine ring)—NH—C(=N—R¹)—N(H)—benzimidazole-phenyl-$R^n$ with positions 1,2,3,4 labeled]

| L' | R¹ | $R^n$ | N | base or salt form | Column 1 compound 48/80 lethality test in rats-ED$_{50}$ in mg/kg body weight | Column 2 gastric lesion test ED$_{50}$ in mg/kg body weight |
|---|---|---|---|---|---|---|
| CH$_2$CN | 4-F—C$_6$H$_4$CH$_2$ | — | 4 | ½H$_2$O | 0.16 | 0.63 |
| CH$_2$CH$_2$OH | 4-F—C$_6$H$_4$CH$_2$ | — | 4 | base | 0.01 | 0.63 |
| CH$_2$CH$_2$NH$_2$ | 4-F—C$_6$H$_4$CH$_2$ | — | 3 | H$_2$O | 0.16 | — |
| CH$_2$CH$_2$OH | 4-F—C$_6$H$_4$CH$_2$ | — | 3 | base | 0.31 | — |
| CH$_2$CN | 4-F—C$_6$H$_4$CH$_2$ | — | 3 | H$_2$O | 0.63 | — |

In view of their antihistaminic and serotonin-antagonistic properties, the compounds of formula (I), the intermediates of formula (XVIII) and their acid-addition salts are very useful in the treatment of allergic diseases such as, for example, allergic rhinitis, allergic conjunctivities, chronic urticaria, allergic astma and the like.

In view of their useful antihistaminic and serotonin-antagonistic acitivity, the subject compounds may be formulated into various pharmaceutical forms for administration purposes. To prepare the pharmaceutical compositions of this invention, an effective amount of the particular compound, in base or acid-addition salt form, as the active ingredient is combined in intimate admixture with a pharmaceutically acceptable carrier, which carrier may take a wide variety of forms depending on the form of preparation desired for administration.

These pharmaceutical compositions are desirably in unitary dosage form suitable, preferably, for administration orally, rectally or by parental injection. For example, in preparing the compositions in oral dosage form, any of the usual pharmaceutical media may be employed, such as, for example, water, glycols, oils, alcohols and the like in the case of oral liquid preparations such as suspensions, syrups, elixirs and solutions: or solid carriers such as starches, sugars, kaolin, lubricants, binders, disintegrating agents and the like in the case of powders, pills, capsules and tablets. Because of their ease in administration, tablets and capsules represent the most advantageous oral dosage unit form, in which case solid pharmaceutical carriers are obviously employed. For parenteral compositions, the carrier will usually comprise sterile water, at least in large part, though other ingredients, for example, to aid solubility, may be included. Injectable solutions, for example, may be prepared in which the carrier comprises saline solution, glucose solution or a mixture of saline and glucose solution. Injectable suspensions may also be prepared in which case appropriate liquid carriers, suspending agents and the like may be employed. Acid addition salts of (I) or (XVIII), due to their increased water solubility over the corresponding base form, are obviously more suitable in the preparation of aqueous compositions.

It is especially advantageous to formulate the aforementioned pharmaceutical compositions in dosage unit form for ease of administration and uniformity of dosage. Dosage unit form as used in the specification and claims herein refers to physically discrete units suitable as unitary dosages, each unit containing a predetermined quantity of active ingredient calculated to produce the desired therapeutic effect in association with the required pharmaceutical carrier. Examples of such dosage unit forms are tablets (including scored or coated tablets), capsules, pills, powder packets, wafers, injectable solutions or suspensions, teaspoonfuls, tabletspoonfuls and the like, and segregated multiples thereof.

The present invention is also related with a method of treating allergic diseases in warm-blooded animals suffering from said allergic diseases by administering an effective anti-allergic amount of a compound of formula (I) or (XVIII) or a pharmaceutically acceptable acid addition salt thereof.

Suitable doses administered daily to subjects are varying from 0.1 to 100 mg, more preferably from 1 to 50 mg.

The following examples are intented to illustrate and not to limit the scope of the present invention. Unless otherwise stated all parts therein are by weight.

EXAMPLES

A. Preparation of Intermediates

The preparation of

N-[1-(2-aminoethyl)-4-piperidinyl]-1-[(4-fluorophenyl)methyl]-1H-benzimidazol-2-amine trihydrochloride;

N-[1-(3-aminopropyl)-4-piperidinyl]-1-[(4-fluorophenyl)methyl]-1H-benzimidazol-2-amine trihydrochloride monohydrate;

1-[(4-fluorophenyl)methyl]-N-[1-[2-[(phenylmethyl)amino]ethyl]-4-piperidinyl]-1H-benzimidazol-2-amine; and N-[1-(2-chloroethyl)-4-piperidinyl]-1-[(4-fluorophenyl)methyl]-1H-benzimidazol-2-amine dihydrochloride is described in U.S. Pat. No. 4,219,559.

EXAMPLE I (a) A mixture of 15.7 parts of 1-chloro-2-nitrobenzene, 9.7 parts of 2-furanmethanamine, 8.4 parts of sodium hydrogen carbonate and 45 parts of N,N-dimethylacetamide was stirred overnight at about 120° C. The reaction mixture was cooled, water was added and the product was extracted with 1,1'-oxybisethane. The extract was dried, filtered and evaporated. The residue was purified by column-chromatography over silica gel using trichloromethane as eluent. The pure fractions were collected and the eluent was evaporated. The oily residue was triturated in petroleumether. The product was filtered off and dried, yielding 15 parts of N-(2-nitrophenyl)-2-furanmethanamine; mp. 85.6° C. (intermediate 1).

(b) A mixture of 40 parts of 5-methyl-2-furanmethanamine, 46 parts of 1-chloro-2-nitrobenzene and 210 parts of N,N-diethylethanamine was stirred and refluxed for 2 days. The reaction mixture was evaporated, water was added and the product was extracted with dichloroethane. The extract was dried, filtered and evaporated. The residue was purified by filtration over silica gel using trichloromethane as eluent. The filtrate was evaporated, yielding 62 parts (89%) of 5-methyl-N-(2-nitrophenyl)-2-furanmethanamine as a residue (intermediate 2).

(c) A mixture of 50 parts of 2-chloro-3-nitropyridine, 32.5 parts of 2-pyridinemethanamine, 53 parts of sodium carbonate and 675 parts of N,N-dimethylacetamide was stirred for 1 hour at 100° C. The reaction mixture was cooled and filtered over Hyflo. The filtrate was poured onto 1000 parts of water and the whole was stirred overnight at room temperature. The product was filtered off and dried, yielding 56.4 parts of N-(3-nitro-2-pyridinyl)-2-pyridinemethanamine; mp. 113.6° C. (intermediate 3).

Following the procedure described in (c) there were also prepared:
N-[(4-fluorophenyl)methyl]-4-nitro-3-pyridinamine, 1-oxide (intermediate 4);
2-nitro-N-(2-thienylmethyl)benzenamine (intermediate 5);
N-(2-nitrophenyl)-3-furanmethanamine (intermediate 6); and
4-fluoro-N-(5-methoxy-2-nitrophenyl)benzenemethanamine (intermediate 7).

EXAMPLE II

A mixture of 62 parts of 5-methyl-N-(2-nitrophenyl)-2-furanmethanamine, 2 parts of a solution of thiophene in methanol 4% and 400 parts of methanol, saturated with ammonia, was hydrogenated at normal pressure and at room temperature with 4 parts of palladium-on-charcoal catalyst 10%. After the calculated amount of hydrogen was taken up, the catalyst was filtered off and the filtrate was evaporated, yielding 50.5 parts (95%) of $N^1$-[(5-methyl-2-furanyl)methyl]-1,2-benzenediamine as a residue (intermediate 8).

In a similar manner there were also prepared:
$N^4$-[(4-fluorophenyl)methyl]-3,4-pyridinediamine; mp. 163.7° C. (intermediate 9);
$N^3$-[(4-fluorophenyl)methyl]-3,4-pyridinediamine monohydrochloride; mp. 208.9° C. (intermediate 10);
$N^2$-(2-pyridinylmethyl)-2,3-pyridinediamine; mp. 134.9° C. (intermediate 11);
N-(3-furanylmethyl)-1,2-benzenediamine as a residue; (intermediate 12);
$N^1$-(2-thienylmethyl)-1,2-benzenediamine as a residue; (intermediate 13);
$N^2$-(2-furanylmethyl)-2,3-pyridinediamine as a residue; (intermediate 14);
N-(2-furanylmethyl)-1,2-benzenediamine as a residue; (intermediate 15); and
$N^2$-[(4-fluorophenyl)methyl]-4-methoxy-1,2-benzenediamine as a residue (intermediate 16).

EXAMPLE III

To a stirred and cooled (0° C.) solution of 8.7 parts of N-[(4-fluorophenyl)methyl]-4-nitro-3-pyridinamine, 1-oxide and 150 parts of trichloromethane was added dropwise a solution of 10.2 parts of phosphor trichloride in 75 parts of trichloromethane. Upon completion, the mixture was allowed to reach room temperature and stirring was continued for 1 hour at reflux temperature. The reaction mixture was cooled and the solvent was evaporated. The residue was stirred in trichloromethane. The product was filtered off and dried, yielding 9 parts of N-[(4-fluorophenyl)methyl]-4-nitro-3-pyridinamine monohydrochloride (intermediate 17).

EXAMPLE IV

A mixture of 3 parts of 2,3-pyridinediamine and 4 parts of 1-(chloromethyl)-4-fluorobenzene was stirred overnight at 120° C. Trichloromethane and a dilute ammonium hydroxide solution were added and the product was extracted. The organic phase was washed with water, dried, filtered and evaporated. The residue was purified by column-chromatography over silica gel using a mixture of trichloromethane and methanol (90:10 by volume) as eluent. The second fraction was collected and the eluent was evaporated, yielding 1.8 parts of $N^3$-[(4-fluorophenyl)methyl]-2,3-pyridinediamine as a residue (intermediate 18).

EXAMPLE V

A mixture of 54 parts of ethyl 4-isothiocyanato-1-piperidinecarboxylate, 48 parts of $N^2$-(2-furanylmethyl)-2,3-pyridinediamine and 450 parts of tetrahydrofuran was stirred and refluxed overnight. The reaction mixture was evaporated and the residue was crystallized from a mixture of 2-propanone and 2,2'-oxybispropane. The product was filtered off and dried, yielding 76 parts (75%) of ethyl 4-[[[2-[(2-furanylmethyl)amino]-3-pyridinyl]aminothioxomethyl]amino]-1-piperidinecarboxylate; m.p. 132.7° C. (intermediate 19)
In a similar manner there were also prepared:
ethyl 4-[[[2-[(2-furanylmethyl)amino]phenyl]aminothioxomethyl]amino]-1-piperidinecarboxylate as a residue (intermediate 20);
ethyl 4-[[[3-[[(4-fluorophenyl)methyl]amino]-2-pyridinyl]aminothioxomethyl]amino]-1-piperidinecarboxylate as a residue (intermediate 21);
ethyl 4-[[[4-[[(4-fluorophenyl)methyl]amino]-3-pyridinyl]aminothioxomethyl]amino]-1-piperidinecarboxylate; mp. 166° C. (intermediate 22);
ethyl 4-[[[3-[[(4-fluorophenyl)methyl]amino]-4-pyridinyl]aminothioxomethyl]amino]-1-piperidinecarboxylate as a residue (intermediate 23);
ethyl 4-[[[2-[(2-pyridinylmethyl)amino]-3-pyridinyl]aminothioxomethyl]amino]-1-piperidinecarboxylate as a residue (intermediate 24);
ethyl 4-[[[2-[(2-thienylmethyl)amino]phenyl]aminothioxomethyl]amino]-1-piperidinecarboxylate as a residue (intermediate 25);
ethyl 4-[[[2-[(3-furanylmethyl)amino]phenyl]aminothioxomethyl]amino]-1-piperidinecarboxylate as a residue (intermediate 26);
ethyl 4-[[[2-[[(5-methyl-2-furanyl)methyl]amino]phenyl]aminothioxomethyl]amino]-1-piperidinecarboxylate as a residue (intermediate 27);
ethyl 4-[[[2-[[(4-methoxyphenyl)methyl]amino]phenyl]aminothioxomethyl]amino]-1-piperidinecarboxylate as a residue (intermediate 28); and
ethyl 4-[[1-[(4-fluorophenyl)methyl]-6-methoxy-1H-benzimidazol-2-yl]amino]-1-piperidinecarboxylate (intermediate 29);

EXAMPLE VI

A mixture of 42.5 parts of ethyl 4-[(phenylmethyl)amino]-1-piperidinecarboxylate, 30 parts of 1-isothiocyanato-2-nitrobenzene and 270 parts of tetrahydrofuran was stirred for 3 hours at room temperature. 2,2'-Oxybispropane was added and stirring was continued overnight. The precipitated product was filtered off and dried, yielding 48.5 parts (68.5%) of ethyl 4-[[[2-nitrophenyl)amino]thioxomethyl](phenylmethyl)amino]-1-piperidinecarboxylate; mp. 140° C.; (intermediate 30).

EXAMPLE VII

A mixture of 48.5 parts of ethyl 4-[[[2-nitrophenyl)amino]thioxomethyl](phenylmethyl)amino]-1-piperidinecarboxylate and 600 parts of methanol, saturated with ammonia, was hydrogenated at normal pressure and at 30° C. with 15 parts of palladium-on-charcoal catalyst 10%. After the calculated amount of hydrogen was taken up, the catalyst was filtered off over Hyflo and the filtrate was evaporated, yielding 47 parts (100%) of ethyl 4-[[[2-aminophenyl)amino]thioxomethyl](phenylmethyl)amino]-1-piperidinecarboxylate as a residue (intermediate 31).

EXAMPLE VIII

A mixture of 74 parts of ethyl 4-[[[2-[(2-furanylmethyl)amino]-3-pyridinyl]aminothioxomethyl]amino]-1-piperidinecarboxylate, 96 parts of mercury (II) oxide, 0.1 parts of sulfur and 800 parts of ethanol was stirred and refluxed for 3 hours. The reaction mixture was filtered over Hyflo and the filtrate was evaporated. The residue was crystallized from acetonitrile, yielding 52.5 parts (79%) of ethyl 4-[[3-(2-furanylmethyl)-3H-imidazo[4,5-b]pyridin-2-yl]amino]-1-piperidinecarboxylate; mp. 149.2° C. (intermediate 32).

Following the same cyclizing-procedure there were also prepared:

ethyl-4-[[1-(2-furanylmethyl)-1H-benzimidazol-2-yl]amino]-1-piperidinecarboxylate; mp. 135.8° C. (intermediate 33);

ethyl 4-[[1-[(4-fluorophenyl)methyl]-1H-imidazo[4,5-b]pyridin-2-yl]amino]-1-piperidinecarboxylate; mp. 212.5° C. (intermediate 34);

ethyl 4-[[1-[(4-fluorophenyl)methyl]-1H-imidazo[4,5-c]pyridin-2-yl]amino]-1-piperidinecarboxylate dihydrochloride monohydrate; (intermediate 35);

ethyl 4-[[3-[(4-fluorophenyl)methyl]-3H-imidazo[4,5-c]pyridin-2-yl]amino]-1-piperidinecarboxylate dihydrochloride monohydrate; mp. 168.6° C. (intermediate 36);

ethyl 4-[[3-(2-pyridinylmethyl)-3H-imidazo[4,5-b]pyridin-2-yl]amino]-1-piperidinecarboxylate; mp. 141.3° C. (intermediate 37);

ethyl 4-[[1-(2-thienylmethyl)-1H-benzimidazol-2-yl]amino]-1-piperidinecarboxylate; mp. 142.7° C. (intermediate 38);

ethyl 4-[[1-(3-furanylmethyl)-1H-benzimidazol-2-yl]amino]-1-piperidinecarboxylate; mp. 150.7° C. (intermediate 39);

ethyl 4-[[1-[(5-methyl-2-furanyl)methyl]-1H-benzimidazol-2-yl]amino]-1-piperidinecarboxylate hemihydrate; mp. 150.1° C. (intermediate 40);

ethyl 4-[[1-[(4-methoxyphenyl)methyl]-1H-benzimidazol-2-yl]amino]-1-piperidinecarboxylate; mp. 157.1° C. (intermediate 41); and ethyl 4-[(1H-benzimidazol-2-yl)(phenylmethyl)amino]-1-piperidinecarboxylate (intermediate 42).

EXAMPLE IX

A mixture of 15.03 parts of ethyl 4-(5-fluoro-1H-benzimidazol-2-ylamino)-1-piperidinecarboxylate, 9 parts of 1-(chloromethyl)-4-fluorobenzene, 5.3 parts of sodium carbonate, 0.2 parts of potassium iodide and 117 parts of N,N-dimethylformamide was stirred and heated over week-end at 70° C. The reaction mixture was cooled and poured onto water. The product was extracted twice with methylbenzene. The combined extracts were dried, filtered and evaporated. The residue was crystallized from a mixture of 2-propanone and 2,2'-oxybispropane. The product was filtered off and dried, yielding 13.4 parts (62.1%) of ethyl 4-[[5(6)-fluoro-1-(4-fluorophenylmethyl)-1H-benzimidazol-2-yl]amino]-1-piperidinecarboxylate; mp. 182.5° C. (intermediate 43).

In a similar manner there were also prepared:

ethyl 4-[[1-[(2-pyridinyl)methyl]-1H-benzimidazol-2-yl]amino]-1-piperidinecarboxylate; mp. 161.5° C. (intermediate 44);

ethyl 4-[[1-(3-pyridinylmethyl)-1H-benzimidazol-2-yl]amino]-1-piperidinecarboxylate; mp. 191.4° C. (intermediate 45);

ethyl 4-[[1-(2-pyrazinylmethyl)-1H-benzimidazol-2-yl]amino]-1-piperidinecarboxylate dihydrobromide monohydrate; mp. 178.5°–179.3° C. (intermediate 46);

ethyl 4-[[1-(4-thiazolylmethyl)-1H-benzimidazol-2-yl]amino]-1-piperidinecarboxylate; mp. 156.2° C. (intermediate 47);

ethyl 4-[[1-[(4-fluorophenyl)methyl]-1H-benzimidazol-2-yl]methylamino]-1-piperidinecarboxylate as a residue (intermediate 48); and ethyl 4-[[1-[(5-methyl-1H-imidazol-4-yl)methyl]-1H-benzimidazol-2-yl]amino]-1-piperidinecarboxylate dihydrochloride; mp. 233.7° C. (intermediate 49).

EXAMPLE X

A mixture of 50 parts of ethyl 4-[[3-(2-furanylmethyl)-3H-imidazo[4,5-b]pyridin-2-yl]amino]-1-piperidinecarboxylate, 50 parts of potassium hydroxide, 400 parts of 2-propanol and 20 drops of water was stirred and refluxed for about 5 hours. The reaction mixture was evaporated and water was added to the residue. The product was extracted twice with 4-methyl-2-pentanone. The combined extracts were dried, filtered and evaporated. The solid residue was stirred in 1,1'-oxybisethane. The product was filtered off and dried, yielding 34 parts (85%) of 3-(2-furanylmethyl)-N-(4-piperidinyl)-3H-imidazo[4,5-b]pyridin-2-amine; mp. 159.0° C. (intermediate 50).

Following the same procedure were also prepared:

1-(2-furanylmethyl)-N-(4-piperidinyl)-1H-benzimidazol-2-amine; mp. 211.0° C. (intermediate 51);

N-(4-piperidinyl)-1-(2-thienylmethyl)-1H-benzimidazol-2-amine; (intermediate 52);

1(3-furanylmethyl)-N-(4-piperidinyl)-1H-benzimidazol-2-amine; (intermediate 53);

1-[(5-methyl-2-furanyl)methyl]-N-(4-piperidinyl)-1H-benzimidazol-2-amine as a residue (intermediate 54);

1-[(4-methoxyphenyl)methyl]-N-(4-piperidinyl)-1H-benzimidazol-2-amine; mp. 178.1° C. (intermediate 55);

1-[(4-fluorophenyl)methyl]-5-methoxy-N-(4-piperidinyl)-1H-benzimidazol-2-amine (intermediate 56);

1-[(4-fluorophenyl)methyl]-N-methyl-N-(4-piperidinyl)-1H-benzimidazol-2-amine dihydrochloride monohydrate; mp. 222.2° C. (intermediate 57);

1-[(4-fluorophenyl)methyl]-6-methoxy-N-(4-piperidinyl)-1H-benzimidazol-2-amine (intermediate 58); and N-(phenylmethyl)-N-(4-piperidinyl)-1H-benzimidazol-2-amine; (intermediate 59).

EXAMPLE XI

A mixture of 30 parts of ethyl 4-[[1-[(2-pyridinyl)methyl]-1H-benzimidazol-2-yl]amino]-1-piperidinecarboxylate and 300 parts of a hydrobromic acid solution 48% in water was stirred and heated for 3 hours at 80° C. The reaction mixture was evaporated and the residue was crystallized from methanol, yielding 41 parts (93.2%) of N-(4-piperidinyl)-1-[(2-pyridinyl)methyl]-1H-benzimidazol-2-amine trihydrobromide; mp. 295.9° C. (intermediate 60).

Following the same procedure there were also prepared:

N-(4-piperidinyl)-1-(3-pyridinylmethyl)-1H-benzimidazol-2-amine trihydrobromide; mp. 260° C. (intermediate 61);

N-(4-piperidinyl)-1-(2-pyrazinylmethyl)-1H-benzimidazol-2-amine trihydrobromide; (intermediate 62);

1-[(4-fluorophenyl)methyl]-N-(4-piperidinyl)-1H-imidazo-[4,5-b]pyridin-2-amine dihydrobromide; mp. +300.6° C. (intermediate 63);

1-[(4-fluorophenyl)methyl]-N-(4-piperidinyl)-1H-imidazo-[4,5-c]pyridin-2-amine dihydrobromide; mp. 279.4° C.

N-(4-piperidinyl)-3-(2-pyridinylmethyl)-3H-imidazo[4,5-b]pyridin-2-amine trihydrobromide; mp. 265.5° C. (intermediate 65);

3-[(4-fluorophenyl)methyl]-N-(4-piperidinyl)-3H-imidazo[4,5-c]pyridin-2-amine dihydrobromide monohydrate; mp. 291.6° C. (intermediate 66);

N-(4-piperidinyl)-1-(4-thiazolylmethyl)-1H-benzimidazol-2-amine dihydrobromide monohydrate; mp. 223.5° C. (intermediate 67); and 1-[(5-methyl-1H-imidazol-4-yl)methyl]-N-(4-piperidinyl)-1H-benzimidazol-2-amine trihydrobromide; mp. 272.1° C. (intermediate 68).

EXAMPLE XII

To 2 parts of a solution of 2 parts of thiophene in 40 parts of ethanol were added 15 parts of ethyl 4-oxo-1-piperidinecarboxylate, 25 parts of 1-(4-fluorophenylmethyl)-N-(4-piperidinyl)-1H-benzimidazol-2-amine and 200 parts of methanol. The whole was hydrogenated at normal pressure and at room temperature with 5 parts of platinum-on-charcoal catalyst 5%. After the calculated amount of hydrogen was taken up, the catalyst was filtered off and the filtrate was evaporated. The residue was purified by column-chromatography over silica gel using a mixture of trichloromethane and methanol (90:10 by volume) as eluent. The pure fractions were collected and the eluent was evaporated. The residue was converted into the hydrochloride salt in 2-propanol and 2-propanone. The salt was filtered off and dried, yielding 13.6 parts of ethyl 4-[1-(4-fluorophenylmethyl)-1H-benzimidazol-2-yl-amino][1,4'-bipiperidine]-1'-carboxylate dihydrochloride monohydrate mp. 260° C. (intermediate 69).

A mixture of 25 parts of 1-(phenylmethyl)-3-piperidinone hydrochloride, 55 parts of 1-[(4-fluorophenyl)methyl]-N-(4-piperidinyl)-1H-benzimidazol-2-amine dihydrobromide, 1 parts of a solution of thiophene in ethanol 4%, 50 parts of potassium acetate and 500 parts of 2-methoxyethanol was hydrogenated at normal pressure and at 50° C. with 5 parts of palldium-on-charcoal catalyst 10%. After the calculated amount of hydrogen was taken up, the catalyst was filtered off and the filtrate was evaporated. The residue was taken up in water and the whole was alkalized with sodium hydroxide. The product was extracted with dichloromethane. The extract was dried, filtered and evaporated. The residue was crystallized twice from acetonitrile. The product was filtered off and dried, yielding 9.75 parts of 1-[(4-fluorophenyl)methyl]-N-[1'-(phenylmethyl)-[1,3'-bipiperidin]-4-yl]-1H-benzimidazol-2-amine; mp. 174.6° C. (intermediate 70).

EXAMPLE XIII

A mixture of 21 parts of ethyl 4-[1-(4-fluorophenylmethyl)-1H-benzimidazol-2-ylamino][1,4'-bipiperidine]-1'-carboxylate and 450 parts of hydrobromic acid solution 48% was stirred and refluxed for 16 hours. The reaction mixture was evaporated. From the residue the free base was liberated in the conventional manner with sodium hydroxide in water and extracted with dichloromethane. The extract was dried, filtered and evaporated, yielding 8 parts (50%) of N-[1-(4-fluorophenylmethyl)-1H-benzimidazol-2-yl][1,4'-bipiperidine]-4-amine as a residue (intermediate 71).

EXAMPLE XIV

A mixture of 11.3 parts of 1-[(4-fluorophenyl)methyl]-N-[1'-(phenylmethyl)-[1,3'-bipiperidin]-4-yl]-1H-benzimidazol-2-amine and 200 parts of methanol was hydrogenated at normal pressure and at room temperature with 2 parts of palladium-on-charcoal catalyst 10%. After the calculated amount of hydrogen was taken up, the catalyst was filtered off and the filtrate was evaporated. The residue was suspended in 2,2'-oxybispropane. The product was filtered off and dried, yielding 8.5 parts (91.5%) of N-([1,3'-bipiperidin]-4-yl)-1-[(4-fluorophenyl)methyl]-1H-benzimidazol-2-amine (intermediate 72).

EXAMPLE XV

A mixture of 2.7 parts of 2-chloroacetonitrile, 19.5 parts of N-(4-piperidinyl)-1-(3-pyridinylmethyl)-1H-benzimidazol-2-amine trihydrobromide, 13 parts of sodium carbonate and 135 parts of N,N-dimethylformamide was stirred and heated for 3 hours at 50° C. The reaction mixture was poured onto water and extracted with dichloromethane. The extract was dried, filtered and evaporated. The residue was crystallized from acetonitrile, yielding 6 parts (50%) of 4-[[1-(3-pyridinylmethyl)-1H-benzimidazol-2-yl]amino]-1-piperidineacetonitrile hemihydrate; mp. 204.5° C. (intermediate 73).

Following the same procedure and using equivalent amounts of the appropriate starting materials there were also prepared:

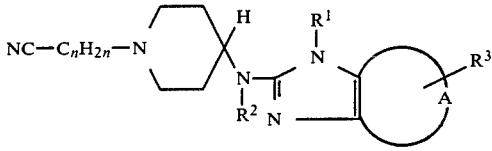

| Comp. No. | n | A | R¹ | R² | R³ | base or salt form | mp. in °C. |
|---|---|---|---|---|---|---|---|
| 74 | 3 | CH=CH—CH=CH | 4-F—C₆H₄CH₂ | H | H | base | 130.5 |
| 75 | 1 | CH=CH—CH=CH | (2-pyridinyl)CH₂ | H | H | base | 152.6 |
| 76 | 1 | CH=CH—CH=CH | 4-F—C₆H₄CH₂ | H | 5(6)-F | base | 176.7 |
| 77 | 1 | N=CH—CH=CH | 4-F—C₆H₄CH₂ | H | H | base | 183.7 |
| 78 | 1 | CH=CH—CH=CH | (2-pyrazinyl)CH₂ | H | H | base | 195.8 |
| 79 | 1 | CH=CH—CH=N | 4-F—C₆H₄CH₂ | H | H | ½H₂O | 173.9 |
| 80 | 1 | CH=CH—CH=CH | (2-fyranyl)CH₂ | H | H | base | 194.4 |
| 81 | 1 | CH=CH—N=CH | 4-F—C₆H₄CH₂ | H | H | H₂O | 188.5 |
| 82 | 1 | N=CH—CH=CH | (2-pyridinyl)CH₂ | H | H | base | 170.0 |
| 83 | 1 | N=CH—CH=CH | (2-furanyl)CH₂ | H | H | base | 157.0 |
| 84 | 1 | CH=CH—CH=CH | (2-thienyl)CH₂ | H | H | base | 191.7 |
| 85 | 1 | CH=N—CH=CH | 4-F—C₆H₄CH₂ | H | H | base | — |
| 86 | 1 | CH=CH—CH=CH | (3-furanyl)CH₂ | H | H | base | 184.0 |
| 87 | 1 | CH=CH—CH=CH | (5-CH₃—2-furanyl)CH₂ | H | H | base | 177.3 |
| 88 | 4 | CH=CH—CH=CH | 4-F—C₆H₄CH₂ | H | H | base | 144.0 |
| 89 | 1 | CH=CH—CH=CH | CH₃ | H | H | base | 212.3 |
| 90 | 1 | CH=CH—CH=CH | C₆H₅CH₂ | H | H | base | 180.4 |
| 91 | 1 | CH=CH—CH=CH | 4-CH₃—C₆H₄CH₂ | H | H | base | 155.2 |
| 92 | 1 | CH=CH—CH=CH | 4-Cl—C₆H₄CH₂ | H | H | base | 180.4 |
| 93 | 1 | CH=CH—CH=CH | 4-CH₃O—C₆H₄CH₂ | H | H | base | 169.9 |
| 94 | 1 | CH=CH—CH=CH | 4-F—C₆H₄CH₂ | H | 5-CH₃O | base | 174.8 |
| 95 | 1 | CH=CH—CH=CH | 4-F—C₆H₄CH₂ | CH₃ | H | base | 157.4 |
| 96 | 1 | CH=CH—CH=CH | 4-F—C₆H₄CH₂ | H | 6-CH₃O | base | 222 |
| 97 | 1 | CH=CH—CH=CH | H | C₆H₅CH₂ | H | base | — |
| 98 | 1 | CH=CH—CH=CH | (5-CH₃—4-imidazolyl)CH₂ | H | H | base | 247.1 |
| 99 | 1 | CH=CH—CH=CH | H | H | H | base | 226 |

In a similar manner there was also prepared: (cis+trans)-4-[[1-[(4-fluoropenyl)methyl]-1H-benzimidazol-2-yl]amino]-3-methyl-1-piperidineacetonitrile; mp. 150.1° C. (intermediate 100).

EXAMPLE XVI

To a stirred mixture of 3.14 parts of 3-furancarboxylic acid, 6 parts of N,N-diethylethanamine and 390 parts of dichloromethane were added 7.2 parts of 2-chloro-1-methylpyridinium iodide. After stirring for 10 minutes at room temperature, 7 parts of 4-[(1H-benzimidazol-2-yl)amino]-1-piperidineacetonitrile were added and the whole was stirred for 1 hour at room temperature. The reaction mixture was washed with water. The organic phase was dried, filtered and evaporated. The residue was crystallized from acetonitrile, yielding 7 parts (74%) of 4-[[1-(3-furanylcarbonyl)-1H-benzimidazol-2-yl]amino]-1-piperidineacetonitrile (intermediate 101).

EXAMPLE XVII

A mixture of 17 parts of 4-[[3-(2-pyridinylmethyl)-3H-imidazo[4,5,-b]pyridin-2-yl]amino]-1-piperidineacetonitrile and 400 parts of methanol, saturated with ammonia, was hydrogenated at normal pressure and at room temperature with 3 parts of Raney-nickel catalyst. After the calculated amount of hydrogen was taken up, the catalyst was filtered off and the filtrate was evaporated. The residue was crystallized from acetonitrile, yielding 15 parts (90%) of N-[1-(2-aminoethyl)-4-piperidinyl]-3-(2-pyridinylmethyl)-3H-imidazo[4,5-b]pyridin-2-amine; mp. 151.1° C. (intermediate 102).

Following the same procedure and using equivalent amounts of the appropriate starting materials there were also prepared:

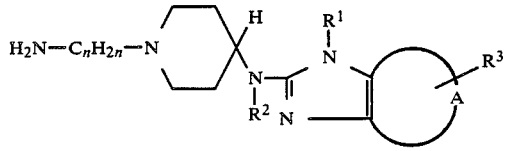

| Comp. No. | n | A | R¹ | R² | R³ | base or salt form | mp. in °C. |
|---|---|---|---|---|---|---|---|
| 103 | 4 | CH=CH—CH=CH | 4-F—C₆H₄CH₂ | H | H | base | — |
| 104 | 2 | N=CH—CH=CH | 4-F—C₆H₄CH₂ | H | H | base | 174.5 |
| 105 | 2 | CH=CH—CH=CH | (2-pyridinyl)CH₂ | H | H | base | 145.1 |
| 106 | 2 | CH=CH—CH=CH | 4-F—C₆H₄CH₂ | H | 5(6)-F | base | 171 |

-continued

Following the same procedure and using equivalent amounts of the appropriate starting materials there were also prepared:

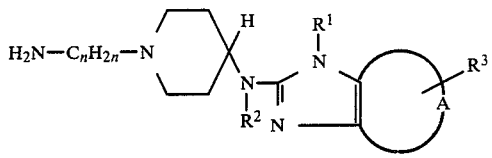

| Comp. No. | n | A | R$^1$ | R$^2$ | R$^3$ | base or salt form | mp. in °C. |
|---|---|---|---|---|---|---|---|
| 107 | 2 | CH=CH—CH=CH | (3-pyridinyl)CH$_2$ | H | H | base | 150.7 |
| 108 | 2 | CH=CH—CH=N | 4-F—C$_6$H$_4$CH$_2$ | H | H | H$_2$O | 116.9 |
| 109 | 2 | CH=CH—CH=CH | (2-pyrazinyl)CH$_2$ | H | H | base | 169.3 |
| 110 | 2 | CH=CH—CH=CH | (2-furanyl)CH$_2$ | H | H | base | 163.0 |
| 111 | 2 | CH=N—CH=CH | 4-F—C$_6$H$_4$CH$_2$ | H | H | H$_2$O | 185.0 |
| 112 | 2 | N=CH—CH=CH | (2-furanyl)CH$_2$ | H | H | 3(E)-2-butene-dioate H$_2$O | 182 |
| 113 | 2 | CH=CH—CH=CH | (2-thienyl)CH$_2$ | H | H | base | 137.1 |
| 114 | 2 | CH=N—CH=CH | 4-F—C$_6$H$_4$CH$_2$ | H | H | base | — |
| 115 | 2 | CH=CH—CH=CH | (3-furanyl)CH$_2$ | H | H | base | 158.1 |
| 116 | 2 | CH=CH—CH=CH | (5-CH$_3$—2-furanyl)CH$_2$ | H | H | base | — |
| 117 | 5 | CH=CH—CH=CH | 4-F—C$_6$H$_4$CH$_2$ | H | H | base | 172.9 |
| 118 | 2 | CH=CH—CH=CH | CH$_3$ | H | H | base | 199.0 |
| 119 | 2 | CH=CH—CH=CH | C$_6$H$_5$CH$_2$ | H | H | base | 131.6 |
| 120 | 2 | CH=CH—CH=CH | 4-Cl—C$_6$H$_4$CH$_2$ | H | H | base | 143.4 |
| 121 | 2 | CH=CH—CH=CH | 4-CH$_3$—C$_6$H$_4$CH$_2$ | H | H | 3(E)-2-butene-dioate | 260 |
| 122 | 2 | CH=CH—CH=CH | 4-CH$_3$O—C$_6$H$_4$CH$_2$ | H | H | base | 129.8 |
| 123 | 2 | CH=CH—CH=CH | 4-F—C$_6$H$_4$CH$_2$ | H | 5-CH$_3$O | base | — |
| 124 | 2 | CH=CH—CH=CH | 4-F—C$_6$H$_4$CH$_2$ | H | 6-CH$_3$O | base | — |
| 125 | 2 | CH=CH—CH=CH | 4-F—C$_6$H$_4$CH$_2$ | CH$_3$ | H | base | — |
| 126 | 2 | CH=CH—CH=CH | (5-CH$_3$—4-imidazolyl)CH$_2$ | H | H | base | 190 and |
| 127 | 2 | CH=CH—CH=CH | H | C$_6$H$_5$CH$_2$ | H | base | 182.8 |

In a similar manner there was also prepared: (cis+trans)-N-[1-(2-aminoethyl)-3-methyl-4-piperidinyl]-1-[(4-fluorophenyl)methyl]-1H-benzimidazol-2-amine; mp. 132.2° C. (intermediate 128).

EXAMPLE XVIII

To 180 parts of tetrahydrofuran were added carefully 2.4 parts of lithium aluminium hydride under nitrogen atmosphere. Then there was added dropwise a solution of 7 parts of 4-[[1-(3-furanylcarbonyl)-1H-benzimidazol-2-yl]amino]-1-piperidineacetonitrile in tetrahydrofuran: temp. rose to 50° C. Upon completion, stirring was continued overnight at reflux temperature. The reaction mixture was cooled in an ice-bath and decomposed by the successive additions of 3 parts of water, 9 parts of a sodium hydroxide solution 15% and 9 parts of water. The whole was filtered over Hyflo and the filtrate was evaporated. The residue was purified by filtration over silica gel using a mixture of trichloromethane and methanol (80:20 by volume) saturated with ammonia, as eluent. The pure fractions were collected and the eluent was evaporated. The residue was crystallized from acetonitrile, yielding 3.6 parts (69.5%) of N-[1-(2-aminoethyl)-4-piperidinyl]-1H-benzimidazol-2-amine; mp. 99.8° C. (intermediate 129).

EXAMPLE XIX

A mixture of 9.25 parts of 1-chloro-2-propanone, 48.6 parts of 1-(4-fluorophenylmethyl)-N-(4-piperidinyl)-1H-benzimidazol-2-amine dihydrobromide, 32 parts of sodium carbonate and 135 parts of N,N-dimethylformamide was stirred and heated overnight at 50° C. The reaction mixture was poured onto water and the product was extracted with 4-methyl-2-pentanone. The extract was dried, filtered and evaporated. The residue was crystallized from 4-methyl-2-pentanone, yielding 15 parts (39.5%) of 1-[4-[[1-[(4-fluorophenyl)methyl]-1H-benzimidazol-2-yl]amino]-1-piperidinyl]-2-propanone (intermediate 130).

A mixture of 5.7 parts of 1-[4-[[1-[(4-fluorophenyl)-methyl]-1H-benzimidazol-2-yl]amino]-1-piperidinyl]-2-propanone, 2.1 parts of hydroxylamine hydrochloride, 20 parts of pyridine, 10 parts of ethanol and 12.5 parts of water was stirred for 3 hours at 65° C. The reaction mixture was poured onto water and the whole was alkalized with sodium hydroxide. The product was filtered off and dried, yielding 5.5 parts (93%) of 1-[4-[[1-[(4-fluorophenyl)methyl]-1H-benzimidazol-2-yl]amino]-1-piperidinyl]-2-propanone, oxime; mp. 202° C. (intermediate 131).

A mixture of 4 parts of 1-[4-[[1-[(4-fluorophenyl)methyl]-1H-benzimidazol-2-yl]amino]-1-piperidinyl]-2-propanone, oxime and 120 parts of methanol, saturated with ammonia, was hydrogenated at normal pressure and at room temperature with 2 parts of Raney-nickel catalyst. After the calculated amount of hydrogen was taken up, the catalyst was filtered off and the filtrate was evaporated. The residue was crystallized from acetonitrile, yielding 1.3 parts (34%) of N-[1-(2-aminopropyl)-4-piperidinyl]-1-[(4-fluorophenyl)methyl]-1H-benzimidazol-2-amine, mp. 178.3° C. (intermediate 132).

EXAMPLE XX

A mixture of 5.4 parts of ethyl (2-chloroethyl)carbamate, 19 parts of N-(4-piperidinyl)-1-(4-thiazolylmethyl)-1H-benzimidazol-2-amine trihydrobromide monohydrate, 15 parts of sodium carbonate, 0.2 parts of sodium iodide and 90 parts of N,N-dimethylacetamide was stirred overnight at about 75° C. Water was added and the product was extracted with 4-methyl-2-pentanone. The extract was dried, filtered and evaporated, yielding 14 parts of ethyl [2-[4-[[1-(4-thiazolylmethyl)-1H-benzimidazol-2-yl]amino]-1-piperidinyl]ethyl]carbamate as an oily residue (intermediate 133)

A mixture of 14 parts of ethyl [2-[4-[[1-(4-thiazolylmethyl)-1H-benzimidazol-2-yl]amino]-1-piperidinyl]ethyl]carbamate and 300 parts of a hydrobromic acid solution 48% in water was stirred and refluxed for 30 minutes. The reaction mixture was evaporated. The sticky residue solidified in a mixture of ethanol and acetonitrile. The product was filtered off and dried, yielding 14 parts of N-[1-(2-aminoethyl)-4-piperidinyl]-1-(4-thiazolylmethyl)-1H-benzimidazol-2-amine trihydrobromide (intermediate 134).

EXAMPLE XXI

To 1 part of a solution of 2 parts of thiophene in 40 parts of ethanol were added 11.3 parts of 1-(4-fluorophenylmethyl)-N-[1-[2-[(phenylmethyl)amino]ethyl]-4-piperidinyl]-1H-benzimidazol-2-amine, 2 parts of paraformaldehyde, 10 parts of potassium acetate and 120 parts of methanol. The whole was hydrogenated at normal pressure and at room temperature with 2 parts of platinum-on-charcoal catalyst 10%. After the calculated amount of hydrogen was taken up, the catalyst was filtered off over Hyflo and the filtrate was evaporated, yielding 9.4 parts of 1-[(4-fluorophenyl)methyl]-N-[1-[2-[methyl(phenylmethyl)amino]ethyl]-4-piperidinyl]-1H-benzimidazol-2-amine as a residue (intermediate 135).

A mixture of 9.4 parts of 1-[(4-fluorophenyl)methyl]-N-[1-[2-(methyl(phenylmethyl)amino]ethyl]-4-piperidinyl]-1H-benzimidazol-2-amine and 120 parts of methanol was hydrogenated at normal pressure and at room temperature with 2 parts of palladium-on-charcoal catalyst 10%. After the calculated amount of hydrogen was taken up, the catalyst was filtered off and the filtrate was evaporated. The residue was converted into the hydrochloride salt in 2-propanol. The salt was filtered off and dried, yielding 6.3 parts (64%) of 1-[(4-fluorophenyl)methyl]-N-[1-[2-(methylamino)ethyl]-4-piperidinyl]-1H-benzimidazol-2-amine trihydrochloride monohydrate; mp. 232.4° C. (intermediate 136).

EXAMPLE XXII

During one hour, gaseous oxirane was bubbled through a stirred mixture of 6 parts of 1-(2-furanylmethyl)-N-(4-piperidinyl)-1H-benzimidazol-2-amine and 40 parts of methanol. Stirring was continued for 3 hours at room temperature. The reaction mixture was evaporated and the oily residue was converted into the (E)-2-butenedioate salt in ethanol and 2-propanone. The salt was filtered off and dried, yielding 6.5 parts of 4-[[1-(2-furanylmethyl)-1H-benzimidazol-2-yl]amino]-1-piperidineethanol (E)-2-butenedioate (2:3) monohydrate; mp. 183.2° C. (intermediate 137).

In a similar manner there was also prepared:
4-[1-(4-fluorophenylmethyl)-1H-benzimidazol-2-ylamino]-1-piperidineethanol; mp. 138.7° C. (intermediate 138)

EXAMPLE XXIII

A mixture of 7.5 parts of N-[1-(2-aminoethyl)-4-piperidinyl]-1-[(4-methoxyphenyl)methyl]-1H-benzimidazol-2-amine and 225 parts of a hydrobromic acid solution 48% in water was stirred and heated over weed-end. After cooling, the precipitated product was filtered off and dried, yielding 7.3 parts (57%) of 4-[[2-[[1-(2-aminoethyl)-4-piperidinyl]amino]-1H-benzimidazol-1-yl]methyl]phenol trihydrobromide monohydrate; mp. >250° C. (intermediate 139).

EXAMPLE XXIV

A mixture of 12 parts of N-[1-(2-aminoethyl)-4-piperidinyl]-1-[(4-fluorophenyl)methyl]-5-methoxy-1H-benzimidazol-2-amine and 150 parts of a hydrobromic acid solution 48% in water was stirred and heated for 48 hours at 80° C. The reaction mixture was evaporated and the residue was suspended in 2-propanol. The product was filtered off and dried, yielding 18.5 parts (95.7%) of 2-[[1-(2-aminoethyl)-4-piperidinyl]amino]-1-[(4-fluorophenyl)methyl]-1H-benzimidazol-5-ol trihydrobromide monohydrate; mp. +250° C. (intermediate 140).

EXAMPLE XXV

To a stirred and cooled (below 10° C.) mixture of 5.04 parts of carbon disulfide, 2.06 parts of N,N'-methanetetraylbis[cyclohexanamine] and 45 parts of tetrahydrofuran was added dropwise a solution of 3.7 parts of N-[1-(2-aminoethyl)-4-piperidinyl]-1-(4-fluorophenylmethyl)-1H-benzimidazol-2-amine in tetrahydrofuran. Upon completion, stirring was continued overnight while the mixture was allowed to reach room temperature. The reaction mixture was evaporated. The residue was purified by column-chromatography over silica gel using a mixture of trichloromethane and methanol (98:2 by volume) as eluent. The pure fractions were collected and the eluent was evaporated, yielding 4 parts (100%) of 1-(4-fluorophenylmethyl)-N-[1-(2-isothiocyanatoethyl)-4-piperidinyl]-1H-benzimidazol-2-amine as a residue (intermediate 141).

In a similar manner there were also prepared:
1-(2-furanylmethyl)-N-[1-(2-isothiocyanatoethyl)-4-piperidinyl]-1H-benzimidazol-2-amine (intermediate 142);
1-[(4-fluorophenyl)methyl]-N-[1-(2-isothiocyanatoethyl)-4-piperidinyl]-1H-imidazo[4,5-b]pyridin-2-amine as a residue (intermediate 143);
N-[1-(2-isothiocyanatoethyl)-4-piperidinyl]-3-(2-pyridinylmethyl)-3H-imidazo[4,5-b]pyridin-2-amine (intermediate 144); and
3-[(4-fluorophenyl)methyl]-N-[1-(2-isothiocyanatoethyl)-4-piperidinyl]-3H-imidazo[4,5-b]pyridin-2-amine as a residue (intermediate 145).

B. Preparation of Final Compounds

EXAMPLE XXVI

1st. Method

A mixture of 1.14 parts of 2-chloropyrimidine, 3.7 parts of N-[1-(2-aminoethyl)-4-piperidinyl]-1-(4-fluorophenylmethyl)-1H-benzimidazol-2-amine, 1.06 parts of sodium carbonate, 0.1 parts of potassium iodide and 135 parts of N,N-dimethylformamide was stirred and heated overnight at 70° C. The reaction mixture was poured onto water and the product was extracted with 4-methyl-2-pentanone. The extract was dried, filtered and evaporated. The residue was purified by column-chromatography over silica gel using a mixture of trichloromethane and methanol (96:4 by volume), saturated with ammonia, as eluent. The pure fractions were collected and the eluent was evaporated. The residue was crystallized from acetonitrile, yielding 1.5 parts (34%) of 1-[(4-fluorophenyl)methyl]-N-[1-[2-[(2- pyrimidinyl)amino]ethyl]-4-piperidinyl]-1H-benzimidazol-2-amine; mp. 168.4° C. (compound 1).

2nd. Method

A mixture of 34.5 parts of 2-chloropyrimidine, 110 parts of N-[1-(2-aminoethyl)-4-piperidinyl]-1-[(4-fluorophenyl)methyl]-1H-benzimidazol-2-amine, 25 parts of sodium hydrogen carbonate and 1200 parts of ethanol was stirred and refluxed overnight. The reaction mixture was cooled and filtered over Hyflo. The filtrate was evaporated. The residue was purified by HPLC over silica gel using a mixture of trichloromethane and methanol (95:5 by volume) saturated with ammonia, as eluent. The pure fractions were collected and the eluent was evaporated. The residue was crystallized from acetonitrile, yielding 82 parts (61%) of 1-[(4-fluorophenyl)methyl]-N-[1-[2-[(2-pyrimidinyl)amino]ethyl]-4-piperidinyl]-1H-benzimidazol-2-amine; mp. 168.4° C. (compound 1).

1[(4-fluorophenyl)methyl]-N-[1-[2-(2-pyrimidinylamino]ethyl]-4-piperidinyl]1H-imidazo[4,5-c]pyridin-2-amine; mp. 203.1° C. (compound 26);

3-(2-pyridinylmethyl)-N-[1-[2-(2-pyrimidinylamino)ethyl]-4-piperidinyl]3H-imidazo[4,5-b]pyridin-2-amine (E)-2-butenedioate (2:3); mp. 181.2° C. (compound 27);

3-(2-furanylmethyl)-N-[1-[2-(2-pyrimidinylamino)ethyl]-4-piperidinyl]-3H-imidazo[4,5-b]pyridin-2-amine; mp. 139.9° C. (compound 28);

3-[(4-fluorophenyl)methyl]-N-[1-[2-[(2-pyrimidinyl)amino]ethyl]-4-piperidinyl]-3H-imidazo[4,5-c]pyridin-2-amine (E)-2-butenedioate (1:2); mp. 198.0° C. (compound 29);

N-[1-[3-[(5-chloro-2-pyridinyl)amino]propyl]-4-piperidinyl]-1-[(4-fluorophenyl)methyl]-1H-benzimidazol-2-amine trihydrochloride monohydrate; mp. 196.5° C. (compound 30);

Following the procedure described in the first method and using equivalent amounts of the appropriate starting materials there were also prepared:

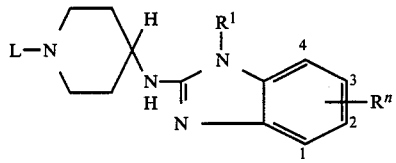

| Comp. No. | L | R¹ | Rⁿ | Base or salt | mp. in °C. |
|---|---|---|---|---|---|
| 2 | 4-[2-pyrimidinyl)NH]butyl | 4-F—C₆H₄CH₂ | H | base | 150.0 |
| 3 | 2-[(3-NO₂—2-pyridinyl)NH]ethyl | 4-F—C₆H₄CH₂ | H | base | 148.1 |
| 4 | 3-[(2-pyrimidinyl)NH]propyl | 4-F—C₆H₄CH₂ | H | base | 143.8 |
| 5 | 2-[(6-Cl—4-pyrimidinyl)NH]ethyl | 4-F—C₆H₄CH₂ | H | 2HCl | 277.9 |
| 6 | 1-(2-pyrimidinyl)-4-piperidinyl | 4-F—C₆H₄CH₂ | H | base | 158.7 |
| 7 | 2-[(2-pyrimidinyl)NH]propyl | 4-F—C₆H₄CH₂ | H | base | 160.8 |
| 8 | 2-[(phenylmethyl)(2-pyrimidinyl)NH]ethyl | 4-F—C₆H₄CH₂ | H | base | 148.7 |
| 9 | 2-(3-NO₂—2-pyridinyl)NH]propyl | 4-F—C₆H₄CH₂ | H | 2HCl. 1½H₂O | 229.3 |
| 10 | 2-[CH₃(2-pyrimidinyl)N]ethyl | 4-F—C₆H₄CH₂ | H | base | 167.2 |
| 11 | 1-(3-NO₂—2-pyridinyl)-4-piperidinyl | 4-F—C₆H₄CH₂ | H | 2H₂O | 108–123 |
| 12 | 1-(2-pyrimidinyl)-3-piperidinyl | 4-F—C₆H₄CH₂ | H | base | 177.1 |
| 13 | 2-[(5-NO₂—2-pyridinyl)NH]ethyl | 4-F—C₆H₄CH₂ | H | base | 175.7 |
| 14 | 2-[(4-NO₂,N—oxide-3-pyridinyl]NH]ethyl | 4-F—C₆H₄CH₂ | H | base | 199.0 |
| 15 | 2-[(2-pyrimidinyl)NH]ethyl | (2-pyridinyl)CH₂ | H | base | 150.8 |
| 16 | 2-[(2-pyrimidinyl)NH]ethyl | 4-F—C₆H₄CH₂ | 2(and 3)F | base | 180.9 |
| 17 | 2-[(2-pyrimidinyl)NH]ethyl | (3-pyridinyl)CH₂ | H | base | 218.9 |
| 18 | 2-[(2-pyrimidinyl)NH]ethyl | (2-pyrazinyl)CH₂ | H | base | 185.8 |
| 19 | 2-[(2-pyrimidinyl)NH]ethyl | (2-thienyl)CH₂ | H | base | 181.5 |
| 20 | 2-[(2-pyrimidinyl)NH]ethyl | (3-furanyl)CH₂ | H | base | 213.3 |
| 21 | 2-[(2-pyrimidinyl)NH]ethyl | (5-CH₃—2-furanyl)CH₂ | H | base | 143.7 |
| 22 | 5-[(2-pyrimidinyl)NH]pentyl | 4-F—C₆H₄CH₂ | H | base | 136.5 |

The following compounds were also prepared following the procedure described in the first method:

3[(4-fluorophenyl)methyl]-N-[1-[2-[(2-pyridinyl)amino]ethyl]-4-piperidinyl]-3H-imidazo[4,5-b]pyridin-2-amine; mp. 181.8° C. (compound 23);

2-[[2-[4-[[3-[(4-fluorophenyl)methyl]-3H-imidazo[4,5-b]pyridin-2-yl]amino]-1-piperidinyl]ethyl]amino]-3-pyridinecarboxamide; mp. 205.4° C. (compound 24);

1-[(4-fluorophenyl)methyl]-N-[1-[2-[(2-pyrimidinyl)amino]ethyl]-4-piperidinyl]-1H-imidazo[4,5-b]pyridin-2-amine; mp. 165.6° C. (compound 25);

6-chloro-N⁴-[2-[4-[[1-[(4-fluorophenyl)methyl]-1H-benzimidazol-2-yl]amino]-1-piperidinyl]ethyl]-4,5-pyrimidinediamine; mp. 216.7° C. (compound 31); and 8-chloro-N-[2-[4-[[1-[(4-fluorophenyl)methyl]-1H-benzimidazol-2-yl]amino]-1-piperidinyl]ethyl]-3-phthalazinamine 2-propanolate (1:1); mp. 139.7° C. (compound 32).

EXAMPLE XXVII

Following the procedure described in the first method of Example XXVI and using N,N-dimethylacetamide as solvent there were also prepared:

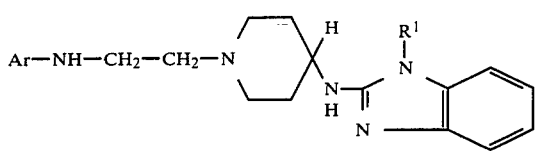

| Comp. No. | Ar | R¹ | Base or salt | mp. in °C. |
|---|---|---|---|---|
| 33 | 2-pyrazinyl | 4-F—C₆H₄CH₂ | base | 209.5 |
| 34 | 2,6-(NH₂)₂—4-pyrimidinyl | 4-F—C₆H₄CH₂ | H₂O | 133.3 |
| 35 | 2-NH₂,6-CH₃—4-pyrimidinyl | 4-F—C₆H₄CH₂ | H₂O | 124.7 |
| 36 | 3-NH₂CO—2-pyridinyl | 4-F—C₆H₄CH₂ | base | 221.2 |
| 37 | 6-Cl—3-pyridazinyl | 4-F—C₆H₄CH₂ | base | 196.8 |
| 38 | 4-quinolinyl | 4-F—C₆H₄CH₂ | base | 227.8 |
| 39 | 5-Br—2-pyridinyl | 4-F—C₆H₄CH₂ | base | 183.3 |
| 40 | 3-Cl—2-pyridinyl | 4-F—C₆H₄CH₂ | base | 124–145 |
| 41 | 3-CH₃—2-quinoxalinyl | 4-F—C₆H₄CH₂ | base | 198.2 |
| 42 | 5-NH₂CO—2-pyridinyl | 4-F—C₆H₄CH₂ | base | 268.2 |
| 43 | 2-pyrimidinyl | (2-furanyl)CH₂ | base | 186.8 |
| 44 | 2-quinolinyl | 4-F—C₆H₄CH₂ | base | 145.2 |
| 45 | 3-Cl—2-pyridinyl | 4-F—C₆H₄CH₂ | 3HCl | — |
| 46 | 3-NH₂Co—2-pyridinyl | (2-furanyl)CH₂ | base | 246.2 |

In a similar manner there were also prepared:

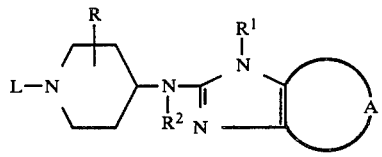

| No. | L | R | R¹ | R² | A | base or salt | mp. °C. |
|---|---|---|---|---|---|---|---|
| 47 | 2-[(3-Cl—2-pyridinyl)amino]ethyl | H | 4-F—C₆H₄CH₂ | H | N=CH—CH=CH | base | 146.5 |
| 48 | 2-[(2-pyrimidinyl)amino]ethyl | H | 5-CH₃—4-imidazolyl-CH₂ | H | CH=CH—CH=CH | base | 184.2 |
| 49 | 2-[(5-Br—2-pyridinyl)amino]ethyl | H | C₆H₅CH₂ | H | CH=CH—CH=CH | base | 164.0 |
| 50 | 2-[(5-Br—2-pyridinyl)amino]ethyl | H | CH₃ | H | CH=CH—CH=CH | base | — |
| 51 | 2-[(5-Br—2-pyridinyl)amino]ethyl | H | 4-CH₃—C₆H₄CH₂ | H | CH=CH—CH=CH | base | — |
| 52 | 2-[(5-Br—2-pyridinyl)amino]ethyl | H | 4-CH₃O—C₆H₄CH₂ | H | CH=CH—CH=CH | base | — |
| 53 | 2-[(5-Cl—2-pyridinyl)amino]ethyl | H | 4-F—C₆H₄CH₂ | H | CH=CH—CH=CH | base | — |
| 54 | 4-[(5-Cl—2-pyridinyl)amino]butyl | H | 4-F—C₆H₄CH₂ | H | CH=CH—CH=CH | base | — |
| 55 | 1-(5-Cl—2-pyridinyl)-4-piperidinyl | H | 4-F—C₆H₄CH₂ | H | CH=CH—CH=CH | base | — |
| 56 | 2-[(5-Cl—2-pyridinyl)methyl amino]ethyl | H | 4-F—C₆H₄CH₂ | H | CH=CH—CH=CH | base | 143.2 |
| 57 | 5-[(5-Cl—2-pyridinyl)amino]pentyl | H | 4-F—C₆H₄CH₂ | H | CH=CH—CH=CH | base | — |
| 58 | 2-[(5-Cl—2-pyridinyl)amino]ethyl | H | 4-F—C₆H₄CH₂ | CH₃ | CH=CH—CH=CH | base | — and |
| 59 | 2-[(2-pyrimidinyl)amino]ethyl | CH₃ | 4-F—C₆H₄CH₂ | H | CH=CH—CH=CH | (cis + trans) 3 HCl | 217.2 |

EXAMPLE XXVIII

A mixture of 3.7 parts of N-[1-(2-aminoethyl)-4-piperidinyl]-1-(4-fluorophenylmethyl)-1H-benzimidazol-2-amine, 1 part of N,N-diethylethanamine and 45 parts of tetrahydrofuran was stirred at −20° C. and there was added dropwise a solution of 1.5 parts of 2,4-dichloropyrimidine in tetrahydrofuran at this temperature. Upon completion, the mixture was allowed to reach slowly room temperature and stirring was continued overnight at room temperature. The precipitate was filtered off and the filtrate was evaporated. The residue was purified by column-chromatography over silica gel using a mixture of trichloromethane and methanol (90:10 by volume), saturated with ammonia, as eluent. The pure fractions were collected and the eluent was evaporated. The residue was converted into the hydrochloride salt in 2-propanol. The salt was filtered off and dried, yielding 1.7 parts of N-[1-[2-[(2-chloro-4-pyrimidinyl)amino]ethyl]-4-piperidinyl]-1-[(4-fluorophenyl)methyl]1H-benzimidazol-2-amine dihydrochloride monohydrate; mp. 287.4° C. (compound 60).

In a similar manner there were also prepared:
N-[1-[2-[(2-chloro-6-methyl-4-pyrimidinyl)amino]ethyl]-4-piperidinyl]-1-[(4-fluorophenyl)methyl]-1H-benzimidazol-2-amine; mp. 124.4° C. (compound 61); and
N-[1-[2-[(4-chloro-6-methyl-2-pyrimidinyl)amino]ethyl]-4-piperidinyl]-1-[(4-fluorophenyl)methyl]-1H-benzimidazol-2-amine; mp. 151.9° C. (compound 62).

EXAMPLE XXIX

A mixture of 3.4 parts of 6-chloro-3-nitro-2-pyridinamine, 7.4 parts of N-[1-(2-aminoethyl)-4-piperidinyl]-1-[(4-fluorophenyl)methyl]1H-benzimidazol-2-amine and 10 parts of 1-methyl-2-pyrrolidinone was stirred and heated for 2 hours at 150° C. The reaction mixture was cooled and taken up in methanol saturated with ammonia. The whole was evaporated and water was added to the residue. The product was extracted three times with 4-methyl-2-pentanone. The combined extracts were dried, filtered and evaporated in vacuo. The residue was purified by column-chromatography over silica gel using a mixture of trichloromethane and methanol (95:5 by volume) as eluent. The pure fractions were collected and the eluent was evaporated. The residue was crystallized from 4-methyl-2-pentanone, yielding 5 parts (50%) of N$^6$-[2-[4-[[1-[(4-fluorophenyl)methyl]1H-benzimidazol-2-yl]amino]-1-piperidinyl]ethyl]-3-nitro-2,6-pyridinediamine; mp. 205.7° C. (compound 63).

EXAMPLE XXX

A mixture of 1.7 parts of 2-chloropyrimidine, 9.66 parts of 2-[[1-(2-aminoethyl)-4-piperidinyl]amino]-1-[(4-fluorophenyl)methyl]-1H-benzimidazol-5-ol trihydrobromide, 5 parts of sodium hydrogen carbonate and 80 parts of ethanol was stirred and refluxed overnight. The reaction mixture was evaporated and the residue was taken up in trichloromethane. The organic phase was washed with water, dried, filtered and evaporated. The residue was crystallized from a mixture of acetonitrile and methanol, yielding 5.2 parts (83%) of 1-[(4-fluorophenyl)methyl]-2-[[1-[2-(2-pyrimidinylamino)ethyl]-4-piperidinyl]amino]-1H-benzimidazol-5-ol; mp. 194.4° C. (compound 64).

In a similar manner there were also prepared:

1-(phenylmethyl)-N-[1-[2-[(2-pyrimidinyl)amino]ethyl]-4-piperidinyl]-1H-benzimidazol-2-amine; mp. 188.3° C. (compound 65);

1-methyl-N-[1-[2-[(2-pyrimidinyl)amino]ethyl]-4-piperidinyl]-1H-benzimidazol-2-amine hemihydrate; mp. 120.9° C. (compound 66);

1-[(4-methylphenyl)methyl]-N-[1-[2-[(2-pyrimidinyl)amino]ethyl]-4-piperidinyl]-1H-benzimidazol-2-amine; mp. 123.6° C. (compound 67);

1-[(4-chlorophenyl)methyl]-N-[1-[2-(2-pyrimidinylamino)ethyl]-4-piperidinyl]-1H-benzimidazol-2-amine; mp. 137.8° C. (compound 68);

1-[(4-methoxyphenyl)methyl]-N-[1-[2-(2-pyrimidinylamino)ethyl]-4-piperidinyl]-1H-benzimidazol-2-amine; mp. 160.4° C. (compound 69);

N-[1-[2-(2-pyrimidinylamino)ethyl]-4-piperidinyl]-1H-benzimidazol-2-amine; mp. 208.6° C. (compound 70);

1-[(4-fluorophenyl)methyl]-5-methoxy-N-[1-[2-(2-pyrimidinylamino)ethyl]-4-piperidinyl]-1H-benzimidazol-2-amine; mp. 160.7° C. (compound 71);

N-[1-[2-(2-pyrimidinylamino)ethyl]-4-piperidinyl]-1-(4-thiazolylmethyl)-1H-benzimidazol-2-amine (E)-2-butenedioate (1:2); mp. 173.9° C. (compound 72);

4-[[2-[[1-[2-(2-pyrimidinylamino)ethyl]-4-piperidinyl]amino]-1H-benzimidazol-1-yl]methyl]phenol; mp. 230.8° C. (compound 73);

1-[(4-fluorophenyl)methyl]-6-methoxy-N-[1-[2-(2-pyrimidinylamino)ethyl]-4-piperidinyl]-1H-benzimidazol-2-amine; mp. 200.1° C. (compound 74);

1-[(4-fluorophenyl)methyl]-N-methyl-N-[1-[2-pyrimidinylamino)ethyl]-4-piperidinyl]-1H-benzimidazol-2-amine; mp. 101.3° C. (compound 75); and N-(phenylmethyl)-N-[1-[2-(2-pyrimidinylamino)ethyl]-4-piperidinyl]-1H-benzimidazol-2-amine; mp. 207.1° C. (compound 76).

EXAMPLE XXXI 5.5 Parts of 4-[1-(4-fluorophenylmethyl)-1H-benzimidazol-2-ylamino]-1-piperidineethanol and 135 parts of N,N-dimethylformamide were stirred at room temperature and 0.75 parts of a sodium hydride dispersion 50% were added. After stirring for one hour at room temperature, 2.5 parts of 2-chloroquinoline were added and the whole was stirred overnight at room temperature. The reaction mixture was poured onto water and the product was extracted with 4-methyl-2-pentanone. The extract was dried, filtered and evaporated. The residue was crystallized from acetonitrile, yielding 4.3 parts (58%) of 1-[(4-fluorophenyl)methyl]-N-[1-[2-(2-quinolinyloxy)ethyl]-4-piperidinyl]-1H-benzimidazol-2-amine; mp. 149.9° C. (compound 77)

In a similar manner there were also prepared:

N-[1-[2-[(5-bromo-2-pyridinyl)oxy]ethyl]-4-piperidinyl]-1-(2-furanylmethyl)-1H-benzimidazol-2-amine; mp. 160.5° C. (compound 78);

1-[(4-fluorophenyl)methyl]-N-[1-[2-[[2-(methylthio)-4-pyrimidinyl]oxy]ethyl]-4-piperidinyl]-1H-benzimidazol-2-amine; mp. 120.6° C. (compound 79);

1-[(4-fluorophenyl)methyl]-N-[1-[2-[(3-methyl-2-quinoxalinyl)oxy]ethyl]-4-piperidinyl]-1H-benzimidazol-2-amine; mp. 168.4° C. (compound 80);

1-[(4-fluorophenyl)methyl]-N-[1-[2-(2-pyrimidinyloxy)ethyl]-4-piperidinyl]-1H-benzimidazol-2-amine; mp. 133.8° C. (compound 81);

N-[1-[2-[(5-bromo-2-pyridinyl)oxy]ethyl]-4-piperidinyl]-1-[(4-fluorophenyl)methyl]-1H-benzimidazol-2-amine; mp. 161.5° C. (compound 82);

1-(2-furanylmethyl)-N-[1-[2-(2-pyrimidinyloxy)ethyl]-4-piperidinyl]-1H-benzimidazol-2-amine (E)-2-butenedioate (1:2); mp. 190.4° C. (compound 83); and 1-[(4-fluorophenyl)methyl]-N-[1-[2-(2-pyridinylmethoxy)ethyl]-4-piperidinyl]-1H-benzimidazol-2-amine (E)-2-butenedioate (1:2); mp. 162° C. (compound 84).

EXAMPLE XXXII

A mixture of 2.7 parts of 5-[(4-chlorophenyl)methyl]-2-(methylthio)-4(1H)-pyrimidinone and 3.67 parts of N-[1-(2-aminoethyl)-4-piperidinyl]-1-[(4-fluorophenyl)methyl]-1H-benzimidazol-2-amine was stirred and heated for 4 hours at 140° C. The reaction mixture was cooled and taken up in trichloromethane. The solution was purified by column-chromatography over silica gel using a mixture of trichloromethane and methanol (96:4 by volume), saturated with ammonia, as eluent. The pure fractions were collected and the eluent was evaporated. The residue was suspended in 1,1'-oxybisethane, yielding 4.5 parts (76.8%) of 5-[(4-chlorophenyl)methyl]-2-[[2-[4-[[1-[(4-fluorophenyl)methyl]-1H-benzimidazol-2-yl]amino]-1-piperidinyl]ethyl]amino]-4(1H)-pyrimidinone monohydrate; mp. 150.6°-158.7° C. (compound 85).

Following the same procedure and using equivalent amounts of the appropriate starting materials there were also prepared:

2-[[2-[4-[[1-[(4-fluorophenyl)methyl]-1H-benzimidazol-2-yl]amino]-1-piperidinyl]ethyl]amino]-6-propyl-4-pyrimidinol; mp. 164.8° C. (compound 86);

2-[[2-[[4-[[1-[(4-fluorophenyl)methyl]-1H-benzimidazol-2-yl]amino]-1-piperidinyl]ethyl]amino]-4(1H)-pyrimidinone; mp. 150.4° C. (compound 87);

2-[[2-[4-[[1-[(4-fluorophenyl)methyl]-1H-benzimidazol-2-yl]amino]1-piperidinyl]ethyl]amino]-4(1H)-quinazolinone; mp. 264.2° C. (compound 88);

2-[[2-[4-[[1-[(4-fluorophenyl)methyl]-1H-benzimidazol-2-yl]amino]-1-piperidinyl]ethyl]amino]-6-(phenylmethyl)-4-(1H)-pyrimidinone; mp. 134.5° C. (compound 89); and 2-[[2-[4-8 [1-[(4-fluorophenyl)methyl]-1H-benzimidazol-2-yl]amino]-1-piperidinyl]ethyl]amino]-6-methyl-4(1H)-pyrimidinone; mp. 143.6° C. (compound 90).

EXAMPLE XXXIII

A mixture of 1.12 parts of 2-pyrimidinethiol, 4.6 parts of N-[1-(2-chloroethyl)-4-piperidinyl]-1-(4-fluorophenylmethyl)-1H-benzimidazol-2-amine dihydrochloride, 4 parts of potassium carbonate and 80 parts of 2-propanone was stirred for 3 days at room temperature. The reaction mixture was filtered and the filtrate was evaporated. The residue was purified by column-chromatography over silica gel using a mixture of trichloromethane and methanol (95:5 by volume) as eluent. The pure fractions were collected and the eluent was evaporated. The residue was crystallized from a mixture of 2-propanone and 2,2'oxybispropane, yielding 1.7 parts (35.8%) of 1-[(4-fluorophenyl)methyl]-N-[1-[2-(2-pyrimidinylthio)ethyl]-4-piperidinyl]-1H-benzimidazol-2-amine; mp. 146.1°-147.7° C. (compound 91).

In a similar manner there was also prepared:

2-[2-[4-[[1-[(4-fluorophenyl)methyl]-1H-benzimidazol-2-yl]amino]-1-piperidinyl]ethylthio]-4(1H)-quinazolinone monohydrate; mp. 133.4° C. (compound 92).

EXAMPLE XXXIV

To 1 part of a solution of 2 parts of thiophene in 40 parts of ethanol were added 8 parts of 1-[(4-fluorophenyl)methyl]-N-[1-[2-[(3-nitro-2-pyridinyl)amino]ethyl]-4-piperidinyl]-1H-benzimidazol-2-amine and 200 parts of methanol. The whole was hydrogenated at normal pressure and at room temperature with 2 parts of platinum-on-charcoal catalyst 5%. After the calculated amount of hydrogen was taken up, the catalyst was filtered off and the filtrate was evaporated. The residue was purified by column-chromatography over silica gel using a mixture of trichloromethane and methanol (90:10 by volume) as eluent. The pure fractions were collected and the eluent was evaporated. The residue was converted into the hydrochloride salt in acetonitrile and 2-propanol. The salt was filtered off and heated in ethanol. After stirring for a while, the whole was cooled. The product was filtered off and dried, yielding 3.4 parts of N²-[2-[4-[[1-[(4-fluorophenyl)methyl]-1H-benzimidazol-2-yl]amino]-1-piperidinyl]ethyl]-2,3-pyridinediamine trihydrochloride; mp. 256.5° C. (compound 93).

EXAMPLE XXXV

A mixture of 3.2 parts of N-[1-[2-[(2-chloro-4-pyrimidinyl)amino]ethyl]-4-piperidinyl]-1-[(4-fluorophenyl)methyl]-1H-benzimidazol-2-amine dihydrochloride, 3 parts of calcium oxide and 120 parts of methanol was hydrogenated at normal pressure and at room temperature with 2 parts of palladium-on-charcoal catalyst 20%. After the calculated amount of hydrogen was taken up, the catalyst was filtered off and the filtrate was evaporated. The residue was crystallized from a mixture of acetonitrile and 2,2'-oxybispropane. The product was filtered off and dried, yielding 1.1 parts of 1-[(4-fluorophenyl)methyl]-N-[1-[2-(4-pyrimidinylamino)ethyl]-4-piperidinyl]-1H-benzimidazol-2-amine hemihydrate; mp. 133.9° C. (compound 94)

In a similar manner there were also prepared:

N-[2-[4-[[1-[(4-fluorophenyl)methyl]-1H-benzimidazol-2-yl]amino]-1-piperidinyl]ethyl]-1-phthalazinamine; mp. 178.1° C. (compound 95);

N⁴-[2-[4-[[1-[(4-fluorophenyl)methyl]-1H-benzimidazol-2-yl]amino]-1-piperidinyl]ethyl]-4,5-pyrimidinediamine; mp. 207.7° C. (compound 96); and N-[1-[(4-fluorophenyl)methyl]-1H-benzimidazol-2-yl]-1'-(2-pyridinyl)-[1,4'-bipiperidin]-4-amine (E)-2-butenedioate (2:3) monohydrate; mp. 226.1° C. (compound 97).

EXAMPLE XXXVI

A mixture of 6 parts of N-[1-[2-[(6-chloro-4-pyrimidinyl)amino]ethyl]-4-piperidinyl]-1-[(4-fluorophenyl)methyl]-1H-benzimidazol-2-amine, 2.5 parts of a sodium methoxide solution 30% and 40 parts of methanol was stirred and refluxed overnight. The reaction mixture was evaporated and water was added to the residue. The product was extracted with 4-methyl-2-pentanone. The extract was dried, filtered and evaporated. The residue was purified by column-chromatography over silica gel using a mixture of trichloromethane and methanol (90:10 by volume) as eluent. The pure fractions were collected and the eluent was evaporated. The residue was crystallized from acetonitrile, yielding 1.4 parts of 1-[(4-fluorophenyl)methyl]-N-[1-[2-[(6-methoxy-4-pyrimidinyl)amino]ethyl]-4-piperidinyl]-1H-benzimidazol-2-amine; mp. 145.8° C. (compound 98).

EXAMPLE XXXVII

A mixture of 4.5 parts of 1-[(4-fluorophenyl)methyl]-N-[1-[2-[(2-pyrimidinyl)amino]ethyl]-4-piperidinyl]-1H-benzimidazol-2-amine, 15 parts of acetic acid anhydride and 140 parts of acetic acid was stirred and refluxed overnight. The reaction mixture was evaporated. The residue was taken up in water and the whole was alkalized with ammonium hydroxide. The product was extracted with dichloromethane. The extract was dried, filtered and evaporated. The residue was purified by HPLC over silica gel using a mixture of methylbenzene and ethanol (90:10 by volume) as eluent. The second fraction was collected and the eluent was evaporated. The residue was converted into the (E)-2-butenedioate salt in methanol. The salt is filtered off and dried, yielding 1.2 parts (16.5%) of N-[2-[4-[[1-[(4-fluorophenyl)methyl]-1H-benzimidazol-2-yl]amino]-1-piperidinyl]ethyl]-N-(2-pyrimidinyl)acetamide (E)-2-butenedioate (1:2); mp. 191.1° C. (compound 99).

EXAMPLE XXXVIII

To a stirred and cooled (0°-10° C.) mixture of 4.45 parts of 1-[(4-fluorophenyl)methyl]-N-[1-[2-[(2-pyrimidinyl)amino]ethyl]-4-piperidinyl]-1H-benzimidazol-2-amine, 1.5 parts of N,N-diethylethanamine and 45 parts of tetrahydrofuran was added dropwise a solution of 1.4 parts of benzoyl chloride in 45 parts of tetrahydrofuran. Upon completion, stirring was continued overnight at room temperature. The reaction mixture was evaporated. The residue was purified by column-chromatography over silica gel using a mixture of trichloromethane and methanol (90:10 by volume) as eluent. The pure fractions were collected and the eluent was evaporated. The residue was converted into the (E)-2-butenedioate salt in ethanol. The salt was filtered off and dried, yielding 4.9 parts of N-[2-[4-[[1-fluorophenyl)methyl]-1H-benzimidazol-2-yl]amino]-1- piperidinyl]ethyl]-N-(2-pyrimidinyl)benzamide (E)-2-butenedioate (1:2); mp. 201.8° C. (compound 100).

EXAMPLE IXL

A mixture of 1.27 parts of 2-ethenylpyrazine, 6.48 parts of 1-[(4-fluorophenyl)methyl]-N-(4-piperidinyl)-1H-benzimidazol-2-amine, 0.3 parts of acetic acid and 40 parts of methanol was stirred and refluxed for 48 hours. The solvent was evaporated. The residue was purified by column-chromatography over silica gel using a mixture of trichloromethane and methanol (88:12 by volume) as eluent. The pure fractions were collected and the eluent was evaporated. The residue was washed with 2,2′-oxybispropane and crystallized from 27 parts of methylbenzene, yielding 2.4 parts of 1-(4-fluorophenylmethyl)-N-[1-[2-(2-pyrazinyl)ethyl]-4-piperidinyl]-1H-benzimidazol-2-amine; mp. 165.3° C. (compound 101).

EXAMPLE XL

A mixture of 1 part of 3-pyridinemethanamine, 3.9 parts of 1-(4-fluorophenylmethyl)-N-[1-(2-isothiocyanatoethyl)-4-piperidinyl]-1H-benzimidazol-2-amine and 45 parts of tetrahydrofuran was stirred for 4 hours at room temperature. The reaction mixture was evaporated in vacuo. The residue was purified by column-chromatography over silica gel using a mixture of trichloromethane and methanol (94:6 by volume) as eluent. The pure fractions were collected and the eluent was evaporated. The residue was crystallized from a mixture of 2-propanone and 2,2′-oxybispropane, yielding 3.4 parts (65.7%) of N-[2-[4-[[1-[(4-fluorophenyl)methyl]-1H-benzimidazol-2-yl]amino]-1-piperidinyl]ethyl]-N′-(3-pyridinylmethyl)thiourea; mp. 147.2° C. (compound 102).

In a similar manner there were also prepared:

N-[2-[4-[[1-[(4-fluorophenyl)methyl]-1H-benzimidazol-2-yl]amino]-1-piperidinyl]ethyl]-N′-(2-pyridinylmethyl)thiourea; mp. 182° C. (compound 103);

N-[2-[4-[[1-[(4-fluorophenyl)methyl]-1H-benzimidazol-2-yl]amino]-1-piperidinyl]ethyl]-N′-(3-pyridinyl)thiourea; mp. 113.5°–117.7° C. (compound 104);

N-[2-[4-[[1-[(4-fluorophenyl)methyl]-1H-benzimidazol-2-yl]amino]-1-piperidinyl]ethyl]-N′-(2-pyridinyl)thiourea; mp. 192.6° C. (compound 105);

N-(4-amino-3-pyridinyl)-N′-[2-[4-[[1-[(4-fluorophenyl)methyl]-1H-benzimidazol-2-yl]amino]-1-piperidinyl]ethyl]thiourea; (compound 106);

N-(3-amino-2-pyridinyl)-N′-[2-[4-[[1-[(4-fluorophenyl)methyl]-1H-benzimidazol-2-yl]amino]-1-piperidinyl]ethyl]thiourea; (compound 107);

N-(4-amino-3-pyridinyl)-N′-[2-[4-[[1-(2-furanylmethyl)-1H-benzimidazol-2-yl]amino]-1-piperidinyl]ethyl]thiourea; (compound 108);

N-(4-amino-3-pyridinyl)-N′-[2-[4-[[1-[(4-fluorophenyl)methyl]-1H-imidazo[4,5-b]pyridin-2-yl]amino]-1-piperidinyl]ethyl]thiourea (compound 109);

N-(4-amino-3-pyridinyl)-N′-[2-[4-[[3-(2-pyridinylmethyl)-3H-imidazo[4,5-b]pyridin-2-yl]amino]-1-piperidinyl]ethyl]thiourea (compound 110); and N-(4-amino-3-pyridinyl)-N′-[2-[4-[[3-[(4-fluorophenyl)methyl]-3H-imidazo[4,5-b]pyridin-2-yl]amino]-1-piperidinyl]ethyl]thiourea (compound 111).

EXAMPLE XLI

To a stirred mixture of 1.7 parts of 2-quinolinecarboxylic acid, 2.02 parts of N,N-diethylethanamine and 195 parts of dichloromethane were added 2.55 parts of 2-chloro-1-methylpyrimidinium iodide and stirring was continued for 15 minutes at room temperature. Then there was added a mixture of 4.4 parts of 4-[1-(4-fluorophenylmethyl)-1H-benzimidazol-2-ylamino]-1-piperidineethanol and 2.02 parts of N,N-diethylethanamine in 130 parts of dichloromethane and the whole was stirred for one hour at room temperature. The reaction mixture was washed with water, dried, filtered and evaporated. The residue was purified by column-chromatography over silica gel using a mixture of trichloromethane and methanol (95:5 by volume) as eluent. The pure fractions were collected and the eluent was evaporated. The residue was converted into the (E)-2-butenedioate salt in 2-propanone. The salt was filtered off and dried, yielding 0.7 parts (9.5%) of [2-[4-[[1-[(4-fluorophenyl)methyl]-1H-benzimidazol-2-yl]amino]-1-piperidinyl]ethyl]-2-quinolinecarboxylate (E)-2-butenedioate (1:2); mp. 197.8° C. (compound 112).

EXAMPLE XLII

To a stirred mixture of 2.1 parts of 3-amino-3-pyrazinecarboxylic acid, 2.8 parts of N,N-dibutylbutanamine and 195 parts of dichloromethane were added 3.83 parts of 2-chloro-1-methylpyridinium iodide. After stirring for 15 minutes at room temperature, 5.5 parts of N-[1-(2-aminoethyl)-4-piperidinyl]-1-[(4-fluorophenyl)methyl]-1H-benzimidazol-2-amine were added and stirring was continued for one hour. The reaction mixture was washed with water, dried, filtered and evaporated. The residue was stirred in 2,2′-oxybispropane. The latter was decanted and the residue was purified by column-chromatography over silica gel using a mixture of trichloromethane and methanol (96:4 by volume) as eluent. The pure fractions were collected and the eluent was evaporated. The residue was crystallized from 1,1′-oxybisethane, yielding 2.8 parts (38%) of 3-amino-N-[2-[4-[[1-[(4-fluorophenyl)methyl]-1H-benzimidazol-2-yl]amino]-1-piperidinyl]ethyl]-2-pyrazinecarboxamide; mp. 156.9° C. (compound 113).

In a similar manner there were also prepared:

N-[2-[4-[[1-[(4-fluorophenyl)methyl]-1H-benzimidazol-2-yl]amino]-1-piperidinyl]ethyl]-2-quinolinecarboxamide (E)-2-butenedioate (1:2); mp. 243.6° C. (compound 114);

2-chloro-N-[2-[4-[[1-[(4-fluorophenyl)methyl]-1H-benzimidazol-2-yl]amino]-1-piperidinyl]ethyl]-3-pyridinecarboxamide (E)-2-butenedioate (1:2) hemihydrate; mp. 211.7° C. (compound 115); and 6-chloro-N-[2-[4-[[1-[(4-fluorophenyl)methyl]-1H-benzimidazol-2-yl]amino]-1-piperidinyl]ethyl]-3-pyridinecarboxamide (E)-2-butenedioate (1:2); mp. 232.7° C. (compound 116).

EXAMPLE XLIII

A mixture of 2.2 parts of 3-bromo-1-propanamine hydrobromide, 4.1 parts of 1-[(4-fluorophenyl)methyl]-N-[1-(2-isothiocyanatoethyl)-4-piperidinyl]-1H-benzimidazol-2-amine, 2.2 parts of sodium carbonate and 135 parts of tetrahydrofuran was stirred overnight at room temperature. The reaction mixture was further stirred and refluxed for 3 hours. The mixture was filtered and the filtrate was evaporated. The residue was purified by column-chromatography over silica gel using a mixture of trichloromethane and methanol (95:5 by volume), saturated with ammonia, as eluent. The pure fractions were collected and the eluent was evaporated. The residue was crystallized from acetonitrile, yielding 2.5 parts of 1-[(4-fluorophenyl)methyl]-N-[1-

[2-[(5,6-dihydro-4H-1,3-thiazin-2-yl)amino]ethyl]-4-piperidinyl]-1H-benzimidazol-2-amine monohydrate; mp. 121.4° C. (compound 117).

What is claimed is:

1. A chemical compound having the formula

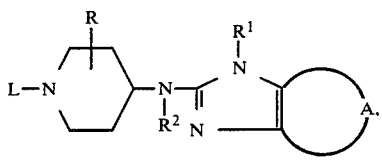

a pharmaceutically acceptable acid addition salt or a stereochemically isomeric form thereof, wherein:

A is a bivalent radical having the formula

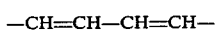 (a),

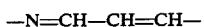 (b),

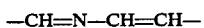 (c),

 (d), or

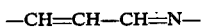 (e), wherein one or two hydrogen atoms in said radicals (a)-(e) may, each independently from each other, be replaced by halo, lower alkyl, lower alkyloxy, trifluoromethyl or hydroxy;

R is a member selected from the group consisting of hydrogen and lower alkyl;

R$^1$ is a member selected from the group consisting of hydrogen, $C_1$–$C_{10}$ alkyl, $C_3$–$C_6$ cycloalkyl, Ar$^1$ and lower alkyl substituted with one or two Ar$^1$ radicals;

R$^2$ is a member selected from the group consisting of hydrogen, lower alkyl, $C_3$–$C_6$ cycloalkyl, (lower alkyl)—CO— and Ar$^2$-lower alkyl;

L is a member selected from the group consisting of a radical of formula

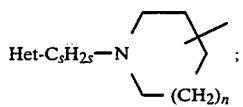 (f)

a radical of formula

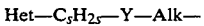 (g); and a radical of formula

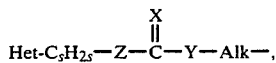 (h)

wherein n is 0 or the integer 1 or 2;
s is 0 or an integer of from 1 to 6 inclusive;
Alk is lower alkanediyl;
Y is O, S, NR$^3$ or a direct bond;
X is O, S, CH—NO$_2$ or NR$^4$;
Z is O, S, NR$^5$ or a direct bond; and
Het is a member selected fro the group consisting of
a pyridinyl radical which is optionally substituted with one or two substituents each independently selected from the group consisting of halo, amino, nitro, cyano, aminocarbonyl, lower alkyl, lower alkyloxy, lower alkylthio, lower alkyloxycarbonyl, hydroxy, lower alkylcarbonyloxy, Ar$^2$-lower alkyl and carboxyl; a pyridinyloxide radical optionally substituted with nitro; a quinolinyl radical which is optionally substituted with a lower alkyl radical; a pyrimidinyl radical which is optionally substituted with one or two substituents each independently selected from the group consisting of halo, amino, hydroxy, lower alkyl, lower alkyloxy, lower alkylthio and (Ar$^2$)-lower alkyl; a quinazolinyl radical which is optionally substituted with a hydroxy radical or a lower alkyl radical; a pyridazinyl radical which is optionally substituted with a lower alkyl radical or a halo radical; a quinoxalinyl radical which is optionally substituted with a lower alkyl radical; a pyrazinyl radical which is optionally substituted with a halo radical, an amino radical or a lower alkyl radical; a phthalazinyl radical which is optionally substituted by a halo radical; and a 5,6-dihydro-4H-1,3-thiazin-2-yl radical, said Het being connected to C$_{s2s}$ on a carbon atom;

said R$^3$ being hydrogen, lower alkyl, (Ar$^2$)lower alkyl, 2-lower alkyloxy-1,2-dioxoethyl or a radical of formula —C(=X)—R$^6$, R$^6$ being hydrogen, lower alkyl, Ar$^2$, Ar$^2$-lower alkyl, lower alkyloxy, Ar$^2$-lower alkyloxy, mono- or di(lower alkyl)amino, Ar$^2$-lower alkylamino or Ar$^2$-lower alkyl(lower alkyl)amino;

said R$^4$ being hydrogen, lower alkyl, cyano, nitro, Ar$^2$-sulfonyl, lower alkylsulfonyl, lower alkylcarbonyl or Ar$^2$-carbonyl; and said R$^5$ being hydrogen or lower alkyl;

provided that Het is other than pyridinyl or mono- or di(lower alkyloxy)pyridinyl where L is a radical (g) wherein Y is NR$^3$ or where L is a radical (h) wherein X is O and Z is NR$^5$ or a direct bond;

wherein Ar$^1$ is a member selected from the group consisting of phenyl, being optionally substituted with up to three substituents each independently selected from the group consisting of halo, hydroxy, nitro, cyano, trifluoromethyl, lower alkyl, lower alkyloxy, lower alkylthio, mercapto, amino, mono- and di(lower alkyl)amino, carboxyl, lower alkyloxycarbonyl and (lower alkyl)—CO—; thienyl; halothienyl; furanyl; lower alkyl substituted furanyl; pyridinyl; pyrazinyl; thiazolyl and imidazolyl optionally substituted by lower alkyl; and wherein Ar$^2$ is a member selected from the group consisting of phenyl being optionally substituted with up to three substituents each independently selected from the group consisting of halo, hydroxy, nitro, cyano, trifluoromethyl, lower alkyl, lower alkyloxy, lower alkylthio, mercapto, amino, mono- and di(lower alkyl)amino, carboxyl, lower alkyloxycarbonyl and (lower alkyl)—CO.

2. A chemical compound according to claim 1 wherein L is a radical (g) or (h).

3. A chemical compound according to claim 2 wherein Het is other than an optionally substituted pyridinyl radical.

4. A chemical compound according to claim 1 wherein the compound is selected from the group consisting of 1-[(4-fluorophenyl)methyl]-N-[1-[2-[(2-pyrimidinyl)amino]ethyl]-4-piperidinyl]-1H-benzimidazol-2-amine, the pharmaceutically acceptable acid addition salts and stereochemically isomeric forms thereof.

5. An anti-allergic composition comprising an inert carrier and an anti-allergic effective amount of a compound having the formula (I)

a pharmaceutically acceptable acid addition salt or a stereochemically isomeric form thereof, wherein:
A is a bivalent radical having the formula —CH=CH—CH=CH— (a), —N=CH—CH=CH— (b), —CH=N—CH=CH— (c), —CH=CH—N=CH— (d), or —CH=CH—CH=N— (e), wherein one or two hydrogen atoms in said radicals (a)-(e) may, each independently from each other, be replaced by halo, lower alkyl, lower alkyloxy, trifluoromethyl or hydroxy;
R is a member selected from the group consisting of hydrogen and lower alkyl;
$R^1$ is a member selected from the group consisting of hydrogen, $C_1$-$C_{10}$ alkyl, $C_3$-$C_6$ cycloalkyl, $Ar^1$ and lower alkyl substituted with one or two $Ar^2$ radicals;
$R^2$ is a member selected from the group consisting of hydrogen, lower alkyl, $C_3$-$C_6$ cycloalkyl, (lower alkyl)—CO— and $Ar^2$-lower alkyl; L is a member selected from the group consisting of
a radical of formula (f)

a radical of formula

Het—$C_sH_{2s}$—Y—Alk— (g); and a radical of formula $$\text{Het-C}_sH_{2s}\text{—Z—}\overset{X}{\underset{\|}{C}}\text{—Y—Alk—,}$$  (h)

wherein
n is 0 or the integer 1 or 2;
s is 0 or an integer of from 1 to 6 inclusive;
Alk is lower alkanediyl;
Y is O, S, $NR^3$ or a direct bond;
X is O, S, CH—$NO_2$ or $NR^4$;
Z is O, S, $NR^5$ or a direct bond; and
Het is a member selected fro the group consisting of
a pyridinyl radical which is optionally substituted with one or two substituents each independently selected from the group consisting of halo, amino, nitro, cyano, aminocarbonyl, lower alkyl, lower alkyloxy, lower alkylthio, lower alkyloxcarbonyl, hydroxy, lower alkylcarbonyloxy, $Ar^2$-lower alkyl and carboxyl; a pyridinyloxide radical optionally substituted with nitro; a quinolinyl radical which is optionally substituted with a lower alkyl radical; a pyrimidinyl radical which is optionally substituted with one or two substituents each independently selected from the group consisting of halo, amino, hydroxy, lower alkyl, lower alkyloxy, lower alkylthio and ($Ar^2$)-lower alkyl; a quinazolinyl radical which is optionally substituted with a hydroxy radical or a lower alkyl radical; a pyridazinyl radical which is optionally substituted with a lower alkyl radical or a halo radical; a quinoxalinyl radical which is optionally substituted with a lower alkyl radical; a pyrazinyl radical which is optionally substituted with a halo radical, an amino radical or a lower alkyl radical; a phthalazinyl radical which is optinally substituted by a halo radical; and a 5,6-dihydro-4H-1,3-thiazin-2-yl radical, said Het being connected to $C_sH_{2s}$ on a carbon atom;
said $R^3$ being hydrogen, lower alkyl, ($Ar^2$)lower alkyl, 2-lower alkyloxy-1,2-dioxoethyl or a radical of formula —C(=X)—$R^6$, $R^6$ being hydrogen, lower alkyl, $Ar^2$, $Ar^2$-lower alkyl, lower alkyloxy, $Ar^2$-lower alkyloxy, mono- or di(lower alkyl)amino, $Ar^2$-lower alkylamino or $Ar^2$-lower alkyl(lower alkyl)amino;
said $R^4$ being hydrogen, lower alkyl, cyano, nitro, $Ar^2$-sulfonyl, lower alkylsulfonyl, lower alkylcarbonyl or $Ar^2$-carbonyl; and
said $R^5$ being hydrogen or lower alkyl;
provided that Het is other than pyridinyl or mono- or di(lower alkyloxy)pyridinyl where L is a radical (g) wherein Y is $NR^3$ or where L is a radical (h) wherein X is O and Z is $NR^5$ or a direct bond;
wherein $Ar^1$ is a member selected from the group consisting of phenyl, being optionally substituted with up to three substituents each independently selected from the group consisting of halo, hydroxy, nitro, cyano, trifluoromethyl, lower alkyl, lower alkyloxy, lower alkylthio, mercapto, amino, mono- and di(lower alkyl)amino, carboxyl, lower alkyloxycarbonyl and (lower alkyl)—CO—; thienyl; halothienyl; furanyl; lower alkyl substituted furanyl; pyridinyl; pyrazinyl; thiazolyl and imidazolyl optionally substituted by lower alkyl; and wherein $Ar^2$ is a member selected from the group consisting of phenyl being optionally substituted with up to three substituents each independently selected from the group consisting of halo, hydroxy, nitro, cyano, trifluoromethyl, lower alkyl, lower alkyloxy, lower alkylthio, mercapto, amino, mono- and di(lower alkyl)amino, carboxyl, lower alkyloxycarbonyl and (lower alkyl)—CO.

6. An anti-allergic composition according to claim 5 wherein L is a radical of formula (g) or (h).

7. An anti-allergic composition according to claim 6 wherein Het is other than an optionally substituted pyridinyl radical.

8. An anti-allergic composition according to claim 5 wherein the compound is selected from the group consisting of 1-[(4-fluorophenyl)methyl]-N-[1-[2-[(2-pyrimidinyl)amino]ethyl]-4-piperidinyl]-1H-benzimidazol-2-amine, the pharmaceutically acceptable acid addition salts and stereochemically isomeric forms thereof.

9. A method of treating allergic diseases in warm-blooded animals suffering from same which method comprises the systemic administration to warm-blooded animals of an effective anti-allergic amount of a compound having the formula

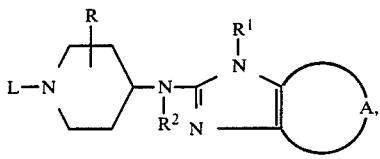

a pharmaceutically acceptable acid addition salt or a stereochemically isomeric form thereof, wherein:

A is a bivalent radical having the formula

| | |
|---|---|
| —CH=CH—CH=CH— | (a), |
| —N=CH—CH=CH— | (b), |
| —CH=N—CH=CH— | (c), |
| —CH=CH—N=CH— | (d), or |
| —CH=CH—CH=N— | (e), | wherein one or two hydrogen atoms in said radicals (a)-(e) may, each independently from each other, be replaced by halo, lower alkyl, lower alkyloxy, trifluoromethyl or hydroxy;

R is a member selected from the group consisting of hydrogen and lower alkyl;

$R^1$ is a member selected from the group consisting of hydrogen, $C_1$-$C_{10}$ alkyl, $C_3$-$C_6$ cycloalkyl, $Ar^1$ and lower alkyl substituted with one or two $Ar^1$ radicals;

$R^2$ is a member selected from the group consisting of hydrogen, lower alkyl, cycloalkyl, (lower alkyl)—CO— and $Ar^2$—lower alkyl;

L is a member selected from the group consisting of a radical of formula

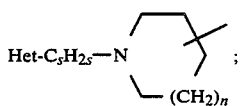 (f)

a radical of formula

Het—$C_sH_{2s}$—Y—Alk—  (g); and a radical of formula

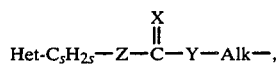 (h)

wherein n is 0 or the integer 1 or 2;
s is 0 or an integer of from 1 to 6 inclusive;
Alk is lower alkanediyl;
Y is O, S, $NR^3$ or a direct bond;
X is O, S, CH—$NO_2$ or $NR^4$;
Z is O, S, $NR^5$ or a direct bond; and
Het is a member selected fro the group consisting of a pyridinyl radical which is optionally substituted with one or two substituents each independently selected from the group consisting of halo, amino, nitro, cyano, aminocarbonyl, lower alkyl, lower alkyloxy, lower alkylthio, lower alkyloxcarbonyl, hydroxy, lower alkylcarbonyloxy, $Ar^2$-lower alkyl and carboxyl; a pyridinyloxide radical optionally substituted with nitro; a quinolinyl radical which is optionally substituted with a lower alkyl radical; a pyrimidinyl radical which is optionally substituted with one or two substituents each independently selected from the group consisting of halo, amino, hydroxy, lower alkyl, lower alkyloxy, lower alkylthio and ($Ar^2$)-lower alkyl; a quinazolinyl radical which is optionally substituted with a hydroxy radical or a lower alkyl radical; a pyridazinyl radical which is optionally substituted with a lower alkyl radical or a halo radical; a quinoxalinyl radical which is optionally substituted with a lower alkyl radical; a pyrazinyl radical which is optionally substituted with a halo radical, an amino radical or a lower alkyl radical; a phthalazinyl radical which is optionally substituted by a halo radical; and a 5,6-dihydro-4H-1,3-thiazin-2-yl radical, said Het being connected to $C_sH_{2s}$ on a carbon atom;

said $R^3$ being hydrogen, lower alkyl, ($Ar^2$)lower alkyl, 2-lower alkyloxy-1,2-dioxoethyl or a radical of formula —C(=X)—$R^6$, $R^6$ being hydrogen, lower alkyl, $Ar^2$, $Ar^2$-lower alkyl, lower alkyloxy, $Ar^2$-lower alkyloxy, mono- or di(lower alkyl)amino, $Ar^2$-lower alkylamino or $Ar^2$-lower alkyl(lower alkyl)amino;

said $R^4$ being hydrogen, lower alkyl, cyano, nitro, $Ar^2$-sulfonyl, lower alkylsulfonyl, lower alkylcarbonyl or $Ar^2$-carbonyl; and said $R^5$ being hydrogen or lower alkyl;

provided that Het is other than pyridinyl or mono- or di(lower alkyloxy)pyridinyl where L is a radical (g) wherein Y is $NR^3$ or where L is a radical (h) wherein X is O and Z is $NR^5$ or a direct bond;

wherein $Ar^1$ is a member selected from the group consisting of phenyl, being optionally substituted with up to three substituents each independently selected from the group consisting of halo, hydroxy, nitro, cyano, trifluoromethyl, lower alkyl, lower alkyloxy, lower alkylthio, mercapto, amino, mono- and di(lower alkyl)amino, carboxyl, lower alkyloxycarbonyl and (lower alkyl)—CO—; thienyl; halothienyl; furanyl; lower alkyl substituted furanyl; pyridinyl; pyrazinyl; thiazolyl and imidazolyl optionally substituted by lower alkyl; and wherein $Ar^2$ is a member selected from the group consisting of phenyl being optionally substituted with up to three substituents each independently selected from the group consisting of halo, hydroxy, nitro, cyano, trifluoromethyl, lower alkyl, lower alkyloxy, lower alkylthio, mercapto, amino, mono- and di(lower alkyl)amino, carboxyl, lower alkyloxycarbonyl and (lower alkyl)—CO.

10. A method according to claim 9 wherein L is a radical of formula (g) or (h).

11. A method according to claim 10 wherein Het is other than an optionally substitued pyridinyl radical.

12. A method according to claim 11 wherein the compound is selected from the group consisting of 1-[(4-fluorophenyl)methyl]-N-[1-[2-[(2-pyrimidinyl)amino]ethyl]-4-piperidinyl]-1H-benzimidazol-2-amine, the pharmaceutically acceptable acid addition salts and stereochemically isomeric forms thereof.

13. A chemical compound according to claim 1, wherein L is pyrimidinyl—$C_sH_{2s}$—Y—Alk—, said pyrimidinyl radical being optionally substituted with one or two substituents each independently selected from the group consisting of halo, amimo, hydroxy, lower alkyl, lower alkyloxy, lower alkylthio, and $(Ar^2)$—lower alkyl.

14. An anti-allergic composition according to claim 5, wherein L is pyrimidinyl—$C_sH_{2s}$—Y—Alk—, said pyrimidinyl radical being optionally substituted with one or two substituents each independently selected from the group consisting of halo, amino, hydroxy, lower alkyl, lower alkyloxy, lower alkylthio, and $(Ar^2)$—lower alkyl.

15. An method according to claim 9, wherein L is pyrimidinyl—$C_sH_{2s}$—Y—Alk—, said pyrimidinyl radical being optionally substituted with one or two substituents each independently selected from the group consisting of halo, amino, hydroxy, lower alkyl, lower alkyloxy, lower alkylthio, and $(Ar^2)$—lower alkyl.

* * * * *

UNITED STATES PATENT AND TRADEMARK OFFICE
CERTIFICATE OF CORRECTION

PATENT NO. : 4,556,660

DATED : December 3, 1985

INVENTOR(S) : Janssens et al.

It is certified that error appears in the above-identified patent and that said Letters Patent is hereby corrected as shown below:

Claim 1, Col. 44, line 23 delete "$C_{s2s}$" and insert -- $C_sH_{2s}$ --.

Signed and Sealed this

Nineteenth Day of August 1986

[SEAL]

Attest:

DONALD J. QUIGG

Attesting Officer

Commissioner of Patents and Trademarks